(12) United States Patent
Matsuura et al.

(10) Patent No.: US 6,183,461 B1
(45) Date of Patent: Feb. 6, 2001

(54) METHOD FOR DELIVERING A MEDICATION

(75) Inventors: David G. Matsuura, Escondido; Walter Dean Gillespie, La Mesa; John Patrick Greelis, Carlsbad; Charles Lowell Parsons, La Jolla; Mikxay Sirivong; Paul F. Zupkas, both of San Diego, all of CA (US)

(73) Assignee: Situs Corporation, Solana Beach, CA (US)

(*) Notice: Under 35 U.S.C. 154(b), the term of this patent shall be extended for 0 days.

(21) Appl. No.: 09/395,415

(22) Filed: Sep. 14, 1999

Related U.S. Application Data

(62) Division of application No. 09/041,475, filed on Mar. 11, 1998.

(51) Int. Cl.[7] .................................................. A61M 31/00
(52) U.S. Cl. .................. 604/502; 604/891.1; 604/93.01; 604/514; 604/517
(58) Field of Search .................... 604/530–532, 604/890.1, 891.1, 93.01, 131, 132, 141, 134, 30, 19, 500, 502, 514, 517

(56) References Cited

U.S. PATENT DOCUMENTS

| | | |
|---|---|---|
| 3,469,578 | 9/1969 | Bierman . |
| 3,498,228 | 3/1970 | Blumle et al. . |
| 3,506,005 | 4/1970 | Gilio et al. . |
| 3,650,093 | 3/1972 | Rosenberg . |
| 3,710,795 | 1/1973 | Higuchi et al. . |
| 3,786,813 | 1/1974 | Michaels . |
| 3,788,322 | 1/1974 | Michaels . |
| 3,797,492 | 3/1974 | Place . |

(List continued on next page.)

FOREIGN PATENT DOCUMENTS

| | | |
|---|---|---|
| 1961 761 | 7/1970 | (DE) . |
| 0 388 234 A1 | 9/1990 | (EP) . |
| 2077 103 | 12/1981 | (GB) . |
| 91/19529 | 12/1991 | (WO) . |
| WO 93/23025 | 11/1993 | (WO) . |
| 94/18952 | 9/1994 | (WO) . |
| WO 96/12477 | 5/1996 | (WO) . |
| WO 96/37202 | 11/1996 | (WO) . |
| 97/41901 | 11/1997 | (WO) . |
| WO 98/43555 | 10/1998 | (WO) . |

OTHER PUBLICATIONS

R.M. Hussain et al. (1996) Effect of oxybutynin on the QTc interval in elderly patients with urinary incontinence. Br J Clin Pharmacol 41:73–75.

S.A. Muller–Lissner et al. (1981) The effect of specific gravity and eating on gastric emptying of slow–release capsules. New England Jour. of Med 304:1365–1366.

Smith et al. (1997) Effect of ditropan on bladder compliance and renal damage in spinal cord injured patients with indwelling catheters. The Jour. Of Urology 157:81.

Primary Examiner—Sharon Kennedy
Assistant Examiner—Deboah Blyveis
(74) Attorney, Agent, or Firm—Knobbe Martens Olsen & Bear, LLP

(57) ABSTRACT

A drug-infusing device is implanted into a body cavity such as a bladder. The device is implanted in an uninflated, low profile state. After insertion into the body cavity, the device is filled with a substance, such as a drug, and assumes an increased profile. After the device is filled, it is allowed to float freely within the body cavity. Alternatively, the device can be tethered to a wall of the body cavity. The device delivers the drug at a controlled rate over an extended period of time. In order to deliver the drug at a controlled rate, the device preferably has a pressure-responsive valving member. The flow resistance of the valving member is responsive to the pressure at which the drug is stored within the infusing device. The resistance of the valving member decreases as the pressure within the infusing device decreases, thereby providing a resultant controlled flow rate.

16 Claims, 17 Drawing Sheets

U.S. PATENT DOCUMENTS

| | | |
|---|---|---|
| 3,845,761 | 11/1974 | Zaffaroni . |
| 3,901,232 | 8/1975 | Michaels et al. . |
| 3,938,515 | 2/1976 | Leeper et al. . |
| 3,944,064 | 3/1976 | Bashaw et al. . |
| 3,948,254 | 4/1976 | Zaffaroni . |
| 3,952,741 | 4/1976 | Baker . |
| 4,155,991 | 5/1979 | Schopflin et al. . |
| 4,201,207 | 5/1980 | Buckles et al. . |
| 4,207,890 | 6/1980 | Mamajek et al. . |
| 4,220,152 | 9/1980 | Dresback . |
| 4,235,236 | 11/1980 | Theeuwes . |
| 4,265,241 | 5/1981 | Portner et al. . |
| 3,993,061 | 11/1976 | O'Leary . |
| 3,993,069 | 11/1976 | Buckles et al. . |
| 3,993,072 | 11/1976 | Zaffaroni . |
| 3,993,073 | 11/1976 | Zaffaroni . |
| 3,995,631 | 12/1976 | Higuchi et al. . |
| 4,012,496 | 3/1977 | Schopflin et al. . |
| 4,034,756 | 7/1977 | Higuchi et al. . |
| 4,055,178 | 10/1977 | Harrigan . |
| 4,067,332 | 1/1978 | O'Leary . |
| 4,111,202 | 9/1978 | Theeuwes . |
| 4,133,315 | 1/1979 | Berman et al. . |
| 4,309,996 | 1/1982 | Theeuwes . |
| 4,351,337 | 9/1982 | Sidman . |
| 4,402,695 | 9/1983 | Wong . |
| 4,482,346 | 11/1984 | Reinicke . |
| 4,485,805 | 12/1984 | Foster, Jr. . |
| 4,486,190 | 12/1984 | Reinicke . |
| 4,524,805 | 6/1985 | Hoffman . |
| 4,553,972 | 11/1985 | Vickery . |
| 4,557,726 | 12/1985 | Reinicke . |
| 4,596,576 | 6/1986 | de Nijs . |
| 4,601,707 | 7/1986 | Albisser et al. . |
| 4,626,244 | 12/1986 | Reinicke . |
| 4,629,449 | 12/1986 | Wong . |
| 4,684,365 | 8/1987 | Reinicke . |
| 4,715,852 | 12/1987 | Reinicke et al. . |
| 4,732,092 | 3/1988 | Millerd . |
| 4,741,733 | 5/1988 | Winchell et al. . |
| 4,798,580 | 1/1989 | DeMeo et al. . |
| 4,813,937 | 3/1989 | Vaillancourt . |
| 4,834,704 | 5/1989 | Reinicke . |
| 4,850,807 | 7/1989 | Frantz . |
| 4,867,743 | 9/1989 | Vaillancourt . |
| 4,871,542 | 10/1989 | Vilhardt . |
| 4,878,905 | 11/1989 | Blass . |
| 4,888,074 | 12/1989 | Pocknell . |
| 4,899,747 | 2/1990 | Garren et al. . |
| 4,904,239 | 2/1990 | Winchell et al. . |
| 4,909,790 | 3/1990 | Tsujikawa et al. . |
| 4,911,717 | 3/1990 | Gaskill, III . |
| 4,915,693 | 4/1990 | Hessel . |
| 4,925,446 | 5/1990 | Garay et al. . |
| 4,936,832 | 6/1990 | Vaillancourt . |
| 4,961,931 | 10/1990 | Wong . |
| 4,968,301 | 11/1990 | di Palma et al. . |
| 5,010,925 | 4/1991 | Atkinson et al. . |
| 5,011,477 | 4/1991 | Winchell et al. . |
| 5,019,047 | 5/1991 | Kriesel . |
| 5,041,094 | 8/1991 | Perego et al. . |
| 5,053,031 | 10/1991 | Borsanyi . |
| 5,061,243 | 10/1991 | Winchell et al. . |
| 5,062,829 | 11/1991 | Pryor et al. . |
| 5,067,943 | 11/1991 | Burke . |
| 5,080,652 | 1/1992 | Sancoff et al. . |
| 5,088,983 | 2/1992 | Burke . |
| 5,098,385 | 3/1992 | Walsh . |
| 5,102,389 | 4/1992 | Hauser . |
| 5,105,983 | 4/1992 | Sancoff et al. . |
| 5,120,315 | 6/1992 | Hessel . |
| 5,147,646 | 9/1992 | Graham . |
| 5,152,747 | 10/1992 | Olivier . |
| 5,167,962 | 12/1992 | Lew et al. . |
| 5,169,390 | 12/1992 | Athayde et al. . |
| 5,176,360 | 1/1993 | Winchell et al. . |
| 5,178,610 | 1/1993 | Tsujikawa et al. . |
| 5,211,632 | 5/1993 | Tsukada . |
| 5,219,334 | 6/1993 | Tsukada . |
| 5,223,266 | 6/1993 | Eckenhoff et al. . |
| 5,224,934 | 7/1993 | Payne et al. . |
| 5,263,935 | 11/1993 | Hessel . |
| 5,272,163 | 12/1993 | Russell et al. . |
| 5,277,912 | 1/1994 | Lowe et al. . |
| 5,284,841 | 2/1994 | Soika et al. . |
| 5,298,025 | 3/1994 | Hessel et al. . |
| 5,301,688 | 4/1994 | Stephen et al. . |
| 5,301,707 | 4/1994 | Hofsteenge . |
| 5,304,123 | 4/1994 | Atala et al. . |
| 5,306,257 | 4/1994 | Zdeb . |
| 5,316,215 | 5/1994 | Mitchell . |
| 5,318,519 | 6/1994 | Wilk . |
| 5,336,194 | 8/1994 | Polaschegg et al. . |
| 5,342,348 | 8/1994 | Kaplan . |
| 5,352,201 | 10/1994 | Jemmott . |
| 5,354,278 | 10/1994 | Kriesel . |
| 5,368,588 | 11/1994 | Bettinger . |
| 5,368,863 | 11/1994 | Eckenhoff et al. . |
| 5,382,598 | 1/1995 | Russell et al. . |
| 5,382,600 | 1/1995 | Jonsson et al. . |
| 5,411,740 | 5/1995 | Lee et al. . |
| 5,429,634 | 7/1995 | Narciso, Jr. . |
| 5,433,709 | 7/1995 | Kriesel . |
| 5,433,710 | 7/1995 | VanAntwerp et al. . |
| 5,445,616 | 8/1995 | Kratoska et al. . |
| 5,474,999 | 12/1995 | Russell et al. . |
| 5,476,434 | 12/1995 | Kalb et al. . |
| 5,500,222 | 3/1996 | Lee et al. . |
| 5,514,096 | 5/1996 | Hiejima et al. . |
| 5,514,103 | 5/1996 | Srisathapat et al. . |
| 5,531,688 | 7/1996 | Hiejima et al. . |
| 5,532,278 | 7/1996 | Aberg et al. . |
| 5,565,465 | 10/1996 | Russell et al. . |
| 5,565,477 | 10/1996 | Russell et al. . |
| 5,567,735 | 10/1996 | Russell et al. . |
| 5,578,005 | 11/1996 | Sancoff et al. . |
| 5,607,418 | 3/1997 | Arzbaecher . |
| 5,630,843 | 5/1997 | Rosenberg . |
| 5,656,032 | 8/1997 | Kriesel et al. . |
| 5,674,895 | 10/1997 | Guittard et al. . |
| 5,677,346 | 10/1997 | Aberg et al. . |
| 5,700,244 | 12/1997 | Kriesel . |
| 5,716,343 | 2/1998 | Kriesel et al. . |
| 5,722,957 | 3/1998 | Steinbach . |
| 5,728,396 | 3/1998 | Peery et al. . |
| 5,743,879 | 4/1998 | Kriesel . |
| 5,746,717 | 5/1998 | Aigner . |
| 5,814,019 | 9/1998 | Steinbach et al. . |
| 5,836,935 | 11/1998 | Ashton et al. . |
| 5,858,017 | 1/1999 | Demopulos et al. . |
| 5,871,478 | 2/1999 | Berrigan . |
| 5,876,377 | 3/1999 | Kriesel . |
| 5,897,530 | 4/1999 | Jackson . |

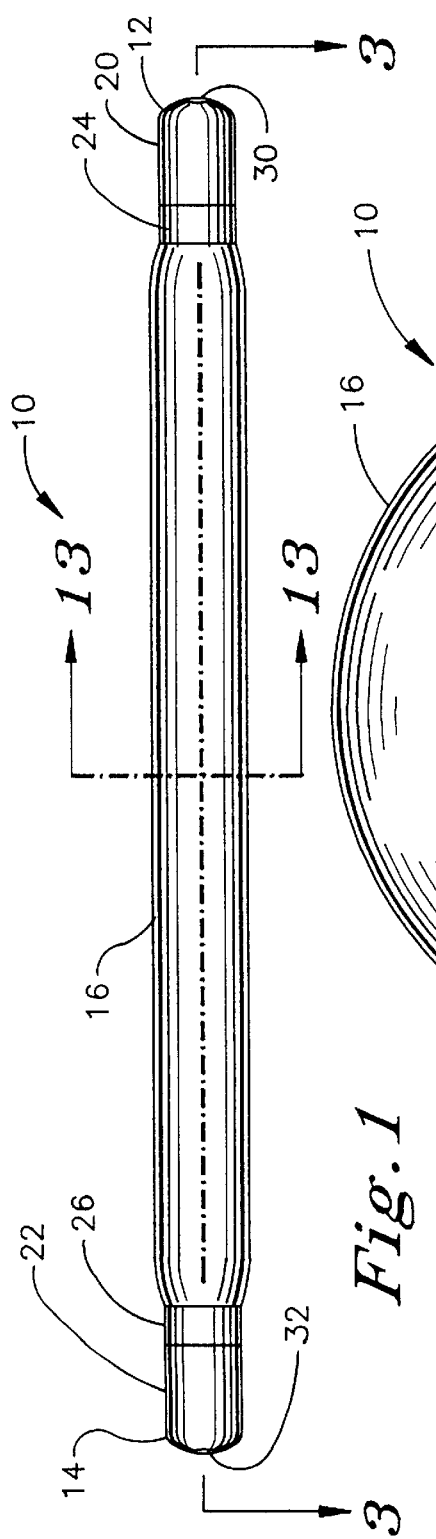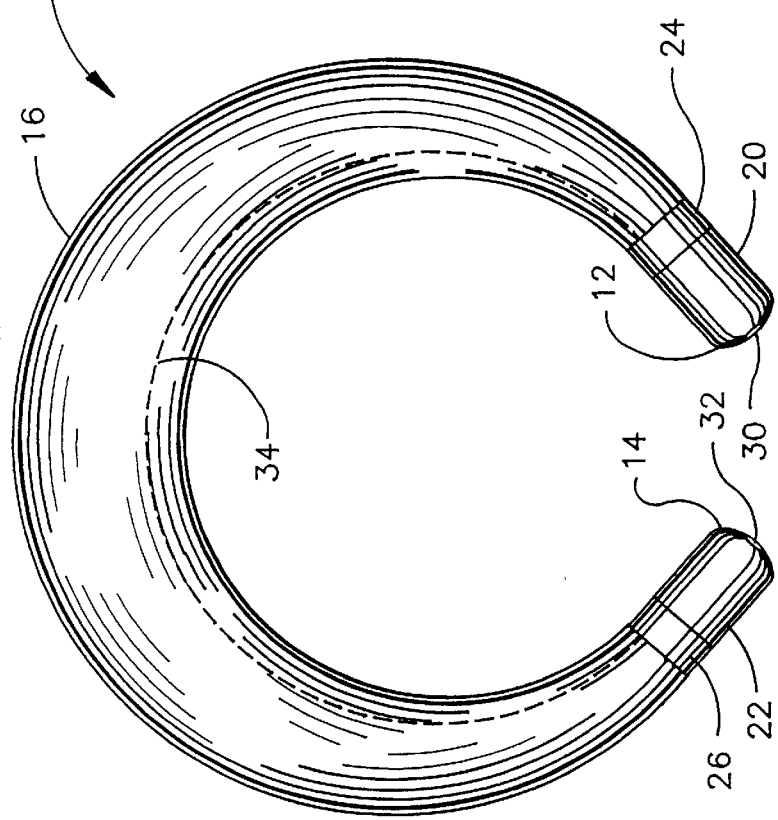
Fig.1
Fig.2

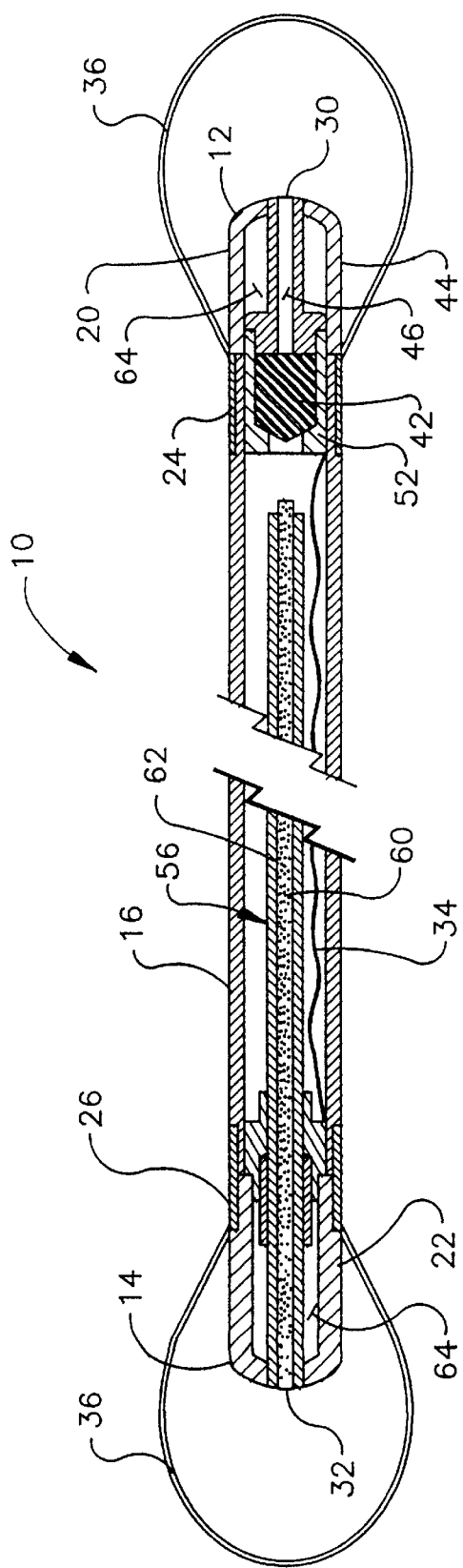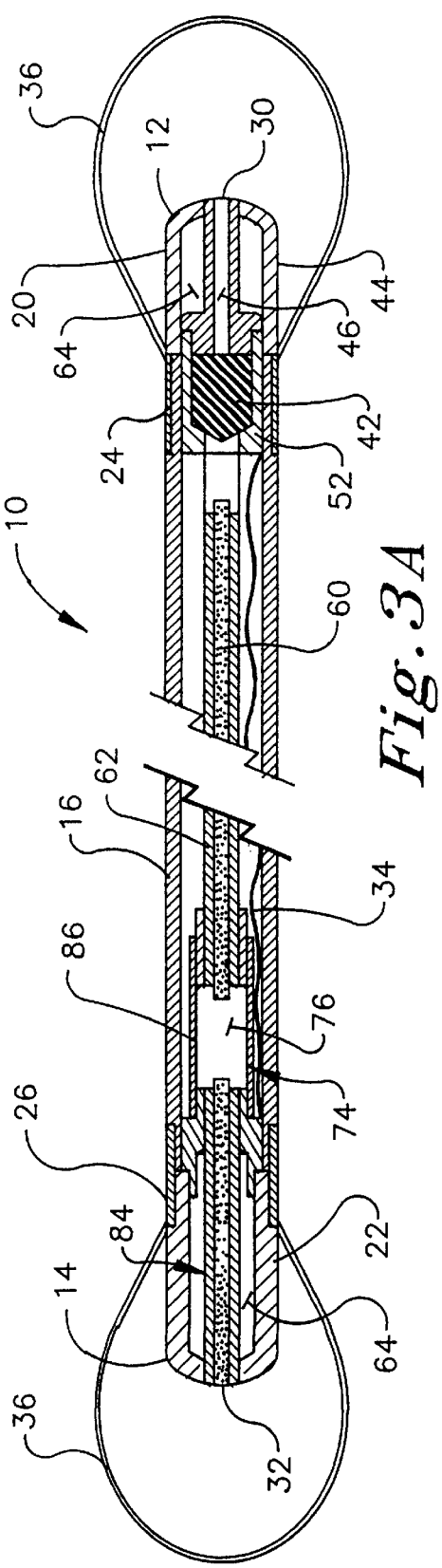

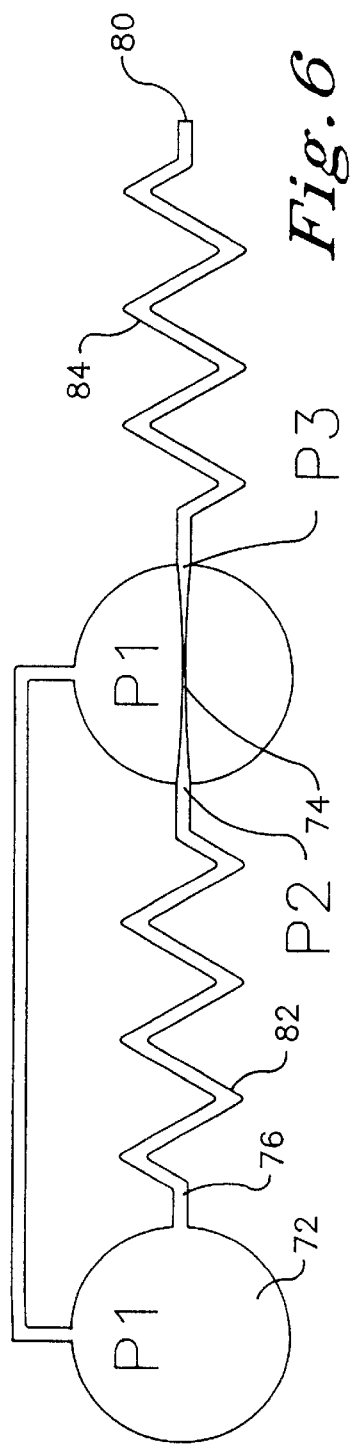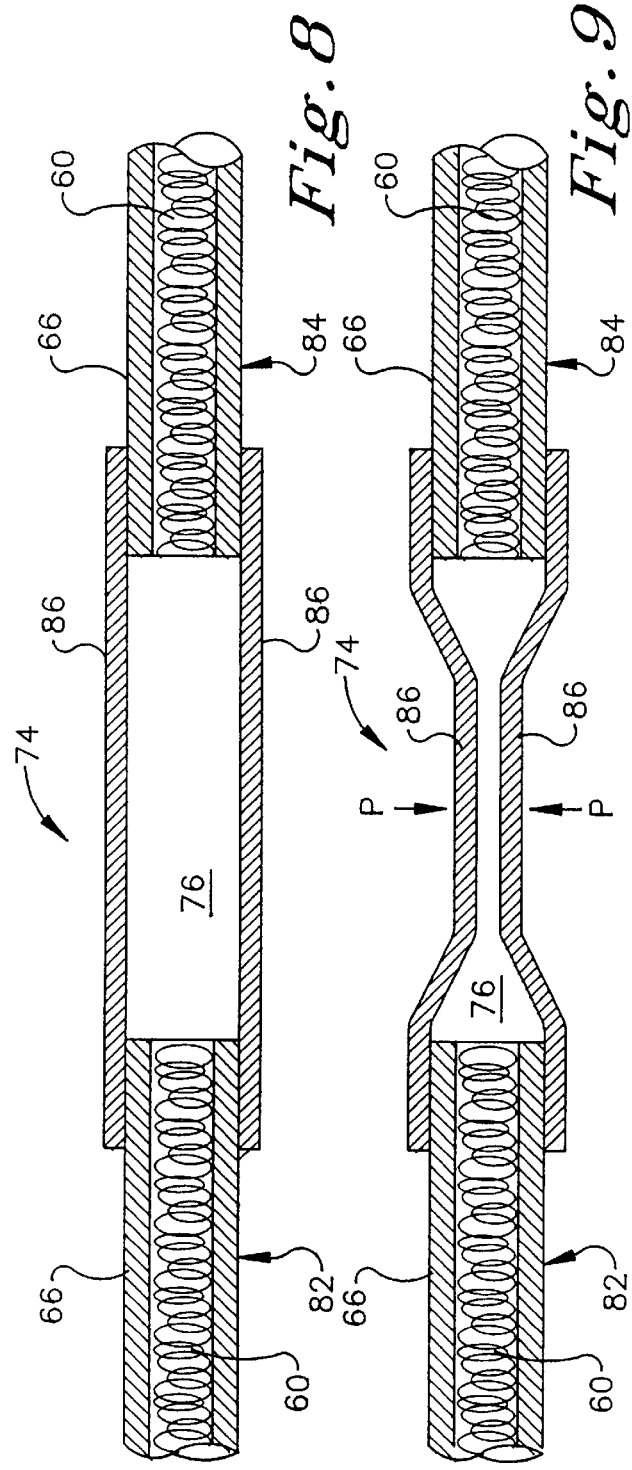

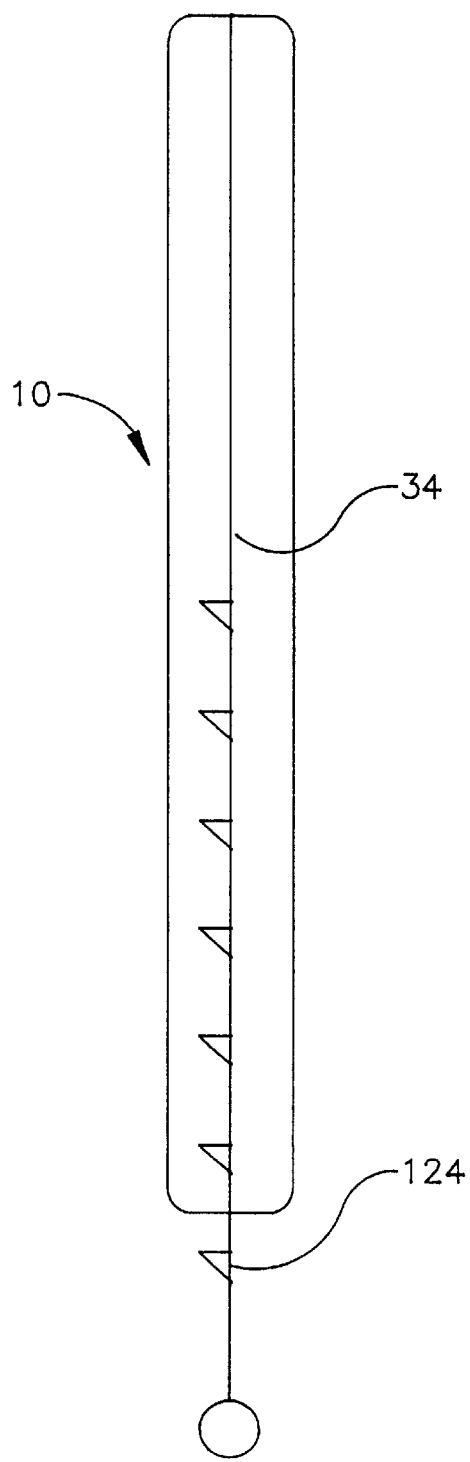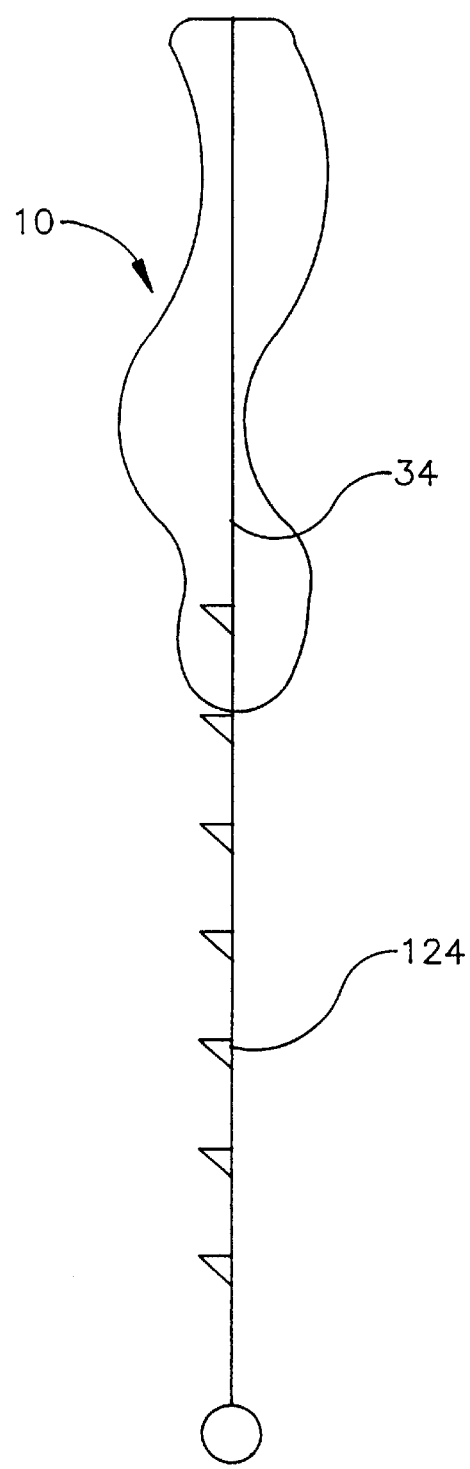
*Fig. 14*  *Fig. 15*

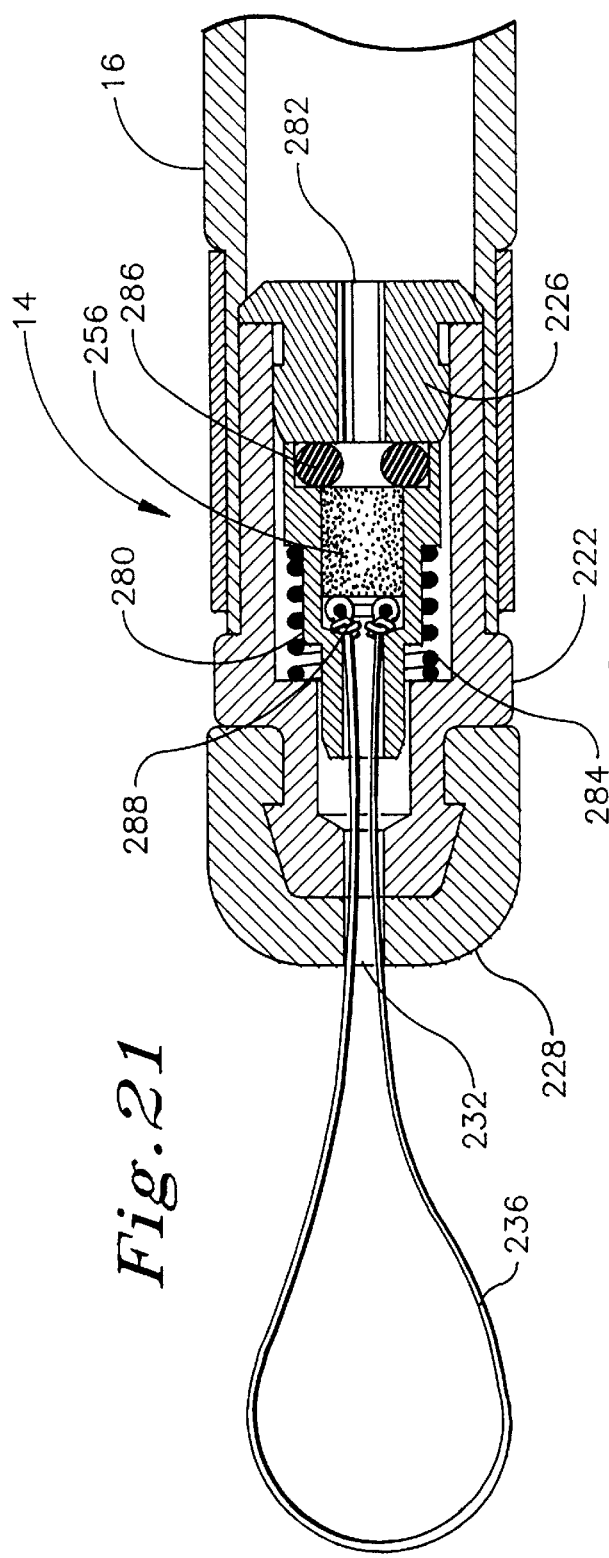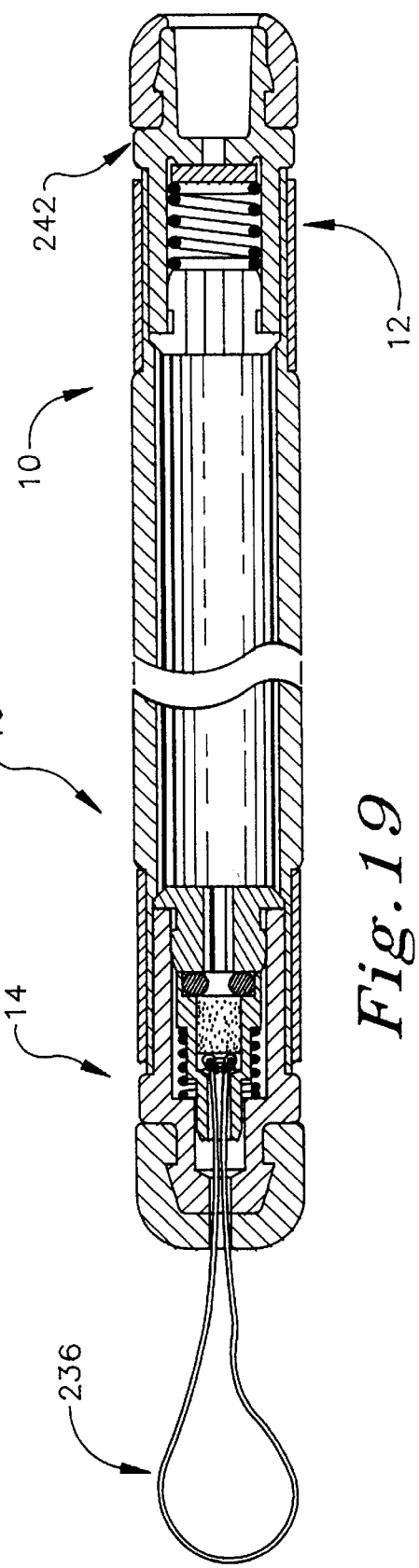
Fig. 21
Fig. 19

METHOD FOR DELIVERING A MEDICATION

RELATED APPLICATION

This application is a divisional application of co-pending U.S. application Ser. No. 09/041,475 filed Mar. 11, 1998, which is hereby incorporated by reference.

BACKGROUND OF THE INVENTION

I. Field of the Invention

The present invention relates to an infuser suitable for use within the bladder and methods of using the infuser.

II. Description of the Related Art

Delivery of drugs to the bladder is typically accomplished systemically. Systemic drug delivery through oral, intravenous, intramuscular, or transdermal administration methods carries with it the obvious drawbacks of any systemic treatment, such as side effects. The drug may also be metabolized or altered by physiological processes, and the ultimate quantity of active drug that reaches the bladder may be reduced. In addition, because many drugs are not well tolerated systemically, the dosage must be limited, thereby reducing the total effective dose that reaches the bladder.

Delivery of drugs to the bladder can also be accomplished by retrograde injection of the drug into the bladder via catheter. Retrograde introduction of drug via a urethral catheter, however, is suitable only for limited situations and has inherent drawbacks. See for example, Bladder Tissue Pharmacokinetics of Intravesical Taxol, Song, D, Wientjes, MG, Au, JL, Cancer Chemotherapy and Pharmacology, 1997, 40(4): 285–92; The Pharmacokinetics of Intravesical and Oral Oxybutynin Chloride, Massad, CA, Kogan, BA, Trigo-Rocha, FE, Journal of Urology, 1992, August, 148(2 Pt 2): 595–7; Advances in Drug Delivery and Targeting, Goldstein, D, Lewis, C, Current Opinion in Oncology, 1991 December 3(6): 1096–104; and Intravesical Hyaluronic Acid in the Treatment of Refractory Interstitial Cystitis, Morales, A, Emerson, L, Nickel, JC, Urology 49 (Suppl 5A): 111–113, 1997. Retrograde introduction of drug via urethral catheter is primarily used only in a hospital or managed care situation. It is not suitable for treatment of chronic urinary-tract conditions.

Stephen et al., U.S. Pat. No. 5,301,688, discloses a method for treating bladder cancers through electromotive administration of drugs into the bladder via a catheter. This type of treatment is suitable primarily for care administered on an in-patient or out-patient basis, not for chronic treatment.

Tsukada, U.S. Pat. No. 5,219,334 discloses an infuser for connection to a catheter that is suitable for long-term delivery of drug into a patient through the catheter. This device requires continuous catheterization in order to function adequately.

Pryor et al., U.S. Pat. No. 5,062,829, discloses a helical device for insertion into a body cavity, e.g., the rumen of a bovine. The helical device includes a drug that can be released over time and further includes a biodegradable portion so that, upon exhaustion of the drug, the device can break up and be naturally eliminated.

Garay et al., U.S. Pat. No. 4,925,446, discloses an infusion device having an annular shape that is suitable for delivering materials into the stomach over a prolonged period of time.

None of these prior art devices address the problem of intravesical drug delivery where drug delivery is intended to continue over a prolonged period of time while the patient maintains an active lifestyle.

Two of the major causes of urge incontinence are detrusor instability and hyperreflexia. Oxybutynin is a pharmacological agent that has been used to treat urge incontinence with some success. This drug is an anticholinergic agent that blocks contraction to the bladder and has direct smooth muscle relaxant properties. Unfortunately, this drug is associated with significant side effects upon oral administration, including dry skin, dry mouth, blurred vision, constipation, and urinary retention. In patients with cardiovascular disease, oxybutynin may lead to tachycardia. Because of the side effects, the accepted oral dose of oxybutynin is limited to 10–15 mg per day.

Interstitial cystitis is a debilitating condition in which the lining of the bladder is irritated, creating a sense of urgency and pain. The condition results in extreme frequency of urination, sometimes as many as 40, 50, or more times per day and can lead to cystectomy. Sufferers of interstitial cystitis can be treated by administration of certain drugs, including pentosanpolysulfate, manufactured by Bene of Munich, Germany and distributed by ALZA Corporation of Palo Alto, Calif. under the trademark ELMIRON. However, there is currently no satisfactory method for delivery of pentosanpolysulfate to a patient over a prolonged period of time while permitting the patient to enjoy a relatively normal lifestyle.

There is a need for a site specific delivery system of drugs for treating bladder and urinary tract disease that will avoid the side effects associated with these pharmacological agents and allow the patient to enjoy an active lifestyle.

SUMMARY OF THE INVENTION

In one aspect of the present invention, there is provided an implantable infusion device comprised of a reservoir containing a drug and a flow-restricted exit port in fluid communication with the drug in the reservoir. The device also is comprised of a coating adapted to inhibit deposition of material on the device when implanted in a body cavity of a mammal. For example, the coating may inhibit deposition of materials present in the urinary tract. The coating may be a sulfated polysaccharide such as pentosanpolysulfate. The coating may be a surface coating on surfaces of the device exposed to the body upon implantation. The coating may be impregnated into the device. In addition or alternatively, a coating may be applied to the device to increase its lubricity.

The flow-restricted exit port may provide delivery of the drug over a period of at least 24 hours, 5 days, 15 days or more. The drug may be in a liquid form and the device may deliver the drug at a rate of less than about 400 µl/hour.

The device may assume a first shape during implantation and a second shape after implantation into the mammal. For example, the device may assume the first shape when empty and the second shape when filled. The first shape may be generally elongated and the second shape may be arcuate. The reservoir of the device may be elastomeric.

The drug within the device may be effective to treat incontinence such as urge incontinence. For example, the drug may be oxybutynin. The drug may also be an anesthetic, analgesic, antibiotic, or anti-cancer agent. Additionally, the drug may be used to treat cystitis.

The device may have a first end and a second end. One of the ends may be buoyant or both the first end and the second end may be buoyant. The device may be sized to fit through a urethra into a mammalian bladder.

Another aspect of the present invention relates to an implantable infusion device comprised of an elongated elastomeric portion having a first end and a second end and adapted to contain and pressurize a liquid. The device may also comprise a flow controller providing an exit port in fluid communication with the liquid in the elastomeric portion. The flow controller may provide for controlled release of the liquid from the device. The device may also comprise a relatively inextensible member connecting the first and second ends of the elastomeric portion in such a way as to allow a relatively straight configuration of the device when unfilled with the liquid and to urge a curved configuration of the device when filled with the liquid. The relatively inextensible member may be inside the elastomeric portion. The elastomeric portion may include a wall and the relatively inextensible member may be associated with the wall. Alternatively, the relatively inextensible member may form a part of the wall. The relatively inextensible member may also be outside of the elastomeric portion.

The implantable infusion device may further comprise an encrustation-resistant coating on the device. For example, the coating may be pentosanpolysulfate. The device may comprise a buoyant portion at the first end. In addition, the device may comprise a buoyant portion at the second end.

Another aspect of the present invention relates to a system for implanting an infusion device. The system is comprised of an elongated infusion device adapted to change shape when filled. The system is also comprised of an introducer suitable for insertion in vivo into a patient and releasably enclosing the infusion device. A conduit is associated with the introducer and releasably attached to the infusion device. The conduit is used to fill the infusion device with liquid in vivo. The conduit may be inside the introducer. The conduit may be attached to a releasable valve on the infusion device. For example, the releasable valve may be a septum seal and the conduit may include a needle for piercing the septum seal. The device may further comprise an extender located within the introducer adapted to push the infusion device distally from the introducer.

Another aspect of the present invention relates to a method for delivering a drug to a patient. The method comprises the steps of delivering an infusion device into the bladder of a patient, releasing the infusion device into the bladder to float freely in the bladder, and infusing a drug into the bladder from the freely floating infusion device. The infusing step may comprise the step of pressurizing the drug with an elastomeric member and releasing the drug at a controlled rate from the infuser. The method may also comprise the step of filling the infusion device with the drug while the device is in the bladder. The filling step may induce the infusion device to change shape. The change of shape may comprise a change in profile. The change of shape may be from a straight configuration when empty to a curved configuration when full. The delivering step may comprise the step of inserting the infusion device through the urethra into the bladder in an unfilled state inside an introducer, then releasing the infusion device from the introducer into the bladder. Alternatively, the delivering step may comprise extending at least a portion of the infusion device from the introducer, and then filling the device within the bladder. In addition, the device may be tethered to the bladder wall.

The method may also comprise the step of removing the infusion device from the bladder after the infusing step. The infusion device used with the method may assume a first shape when empty and a second shape when filled. The removing step may comprise the step of changing the shape of the infusion device from the second shape to the first shape, and then directing the infusion device out of the urethra. The change from the second shape to the first shape may be accomplished by allowing drug in the device to be depleted by the infusing step. The change from the second shape to the first shape may be accomplished by opening a passageway in the device to allow any remaining drug in the device to exit the device. In this case, the method may further comprise the step of directing drug from the passageway through a conduit and out of the bladder. Removing the device may comprise passing the device out of the urethra with a flow of urine. Alternatively, removing the device may comprise capturing and then withdrawing the device.

Infusing a drug into the bladder may comprise controlling the rate of flow of drug from the device into the bladder. Controlling the flow of drug may be accomplished by means of a pressure-responsive valve. For example, the drug may be under pressure and the pressure-responsive valve may control the flow by varying the area of a flow channel in inverse proportion to the pressure of the drug. In addition, the control of the flow may be further accomplished by a flow-resistive element positioned in a fluid flow path upstream of the pressure-responsive valve, thereby reducing the pressure of the drug entering the pressure-responsive valve.

The infusing step of the method may comprise infusing the drug into the bladder for at least about 5 days. The drug used with the method may be used to treat incontinence such as urge incontinence. For example, the drug may be oxybutynin. The drug may also be used to treat pain, neuralgia or cystitis. The drug may be an antibiotic or an anti-cancer drug.

Another aspect of the present invention relates to an infusion device comprised of a housing, a drug inside the housing, a flow controller for controlling the rate at which drug may be released from the housing, and a coating of pentosanpolysulfate on the device. The drug may be pressurized and the flow controller may be pressure-responsive. The flow controller may comprise a first pressure reducing element, a second pressure reducing element, and a flow channel through the first and second pressure reducing elements. The second pressure reducing element may alter a cross-sectional area of the flow path in a manner inversely related to the pressure of the drug.

In yet another aspect of the present invention, an implantable infusion device may comprise an elongated reservoir having a first shape wherein a cross-sectional diameter of the elongated reservoir permits the elongated reservoir to be passed through a mammalian urethra. The elongated reservoir may be configured to expand to a second shape to hold a pressurized fluid substance. A check valve assembly may be disposed at a first end of the elongated reservoir and configured to admit the pressurized fluid substance into the elongated reservoir while the elongated reservoir is within a mammalian bladder. A flow-restricted exit port may be configured to dispense the pressurized fluid substance from the elongated reservoir while the elongated reservoir is within the mammalian bladder. In addition, the device may comprise a tethering means for tethering the device to a bladder wall. The first shape of the device may have a linear configuration with at least one axis of symmetry and the second shape may have a curved configuration that has no axial symmetry.

The flow-restricted exit port may provide a means of rapidly purging the pressurized fluid substance from the elongated reservoir. The device may comprise a capture member which is incorporated into a release mechanism that is configured to allow the flow-restricted exit port to rapidly purge the pressurized fluid substance from the elongated reservoir. The flow-restricted exit port may be configured to mate with a sheath that is introduced into the mammalian bladder such that the pressurized fluid substance is rapidly dispensed through a channel of the sheath rather than into the mammalian bladder. The pressured fluid substance may be a diagnostic tool. The check valve assembly may comprise an floating disc which is biased to occlude an input channel. The device may comprise a means for tethering the device to the bladder wall. In addition, the device may comprise one or more of the features previously enumerated.

BRIEF DESCRIPTION OF THE DRAWINGS

FIG. 1 is a perspective view of an intravesical infuser in uninflated form.

FIG. 2 is a perspective view of an infuser according to the present invention, wherein the infuser is pressurized or inflated with a fluid, causing it to undergo a shape change.

FIG. 3 is a longitudinal cross-section of the intravesical infuser of FIG. 1, taken along the line 3—3.

FIG. 3A is a longitudinal cross-section of an alternative embodiment of the infuser of FIG. 1, taken along the line 3—3.

FIG. 6 is a schematic representation of a pressure-responsive valve for use in the present invention.

FIG. 8 is a longitudinal cross-section of the pressure-responsive valve of FIG. 7, taken along the line 8—8.

FIG. 9 corresponds to the pressure-responsive valve as illustrated in FIG. 8, further illustrating the reduction in cross-sectional flow area upon the application of an external pressure P.

FIG. 14 is a schematic longitudinal cross-section of an intravesical infuser of the present invention, illustrating an alternative use of a tensile member.

FIG. 15 corresponds to FIG. 14, illustrating the application of tension to tensile member to change the shape of the infuser.

FIG. 19 is a longitudinal cross-section of an alternate embodiment of the intravesical infuser.

FIG. 21 is a detailed view of the distal end of the infuser shown in FIG. 19.

DETAILED DESCRIPTION OF THE INVENTION

Figure 4:
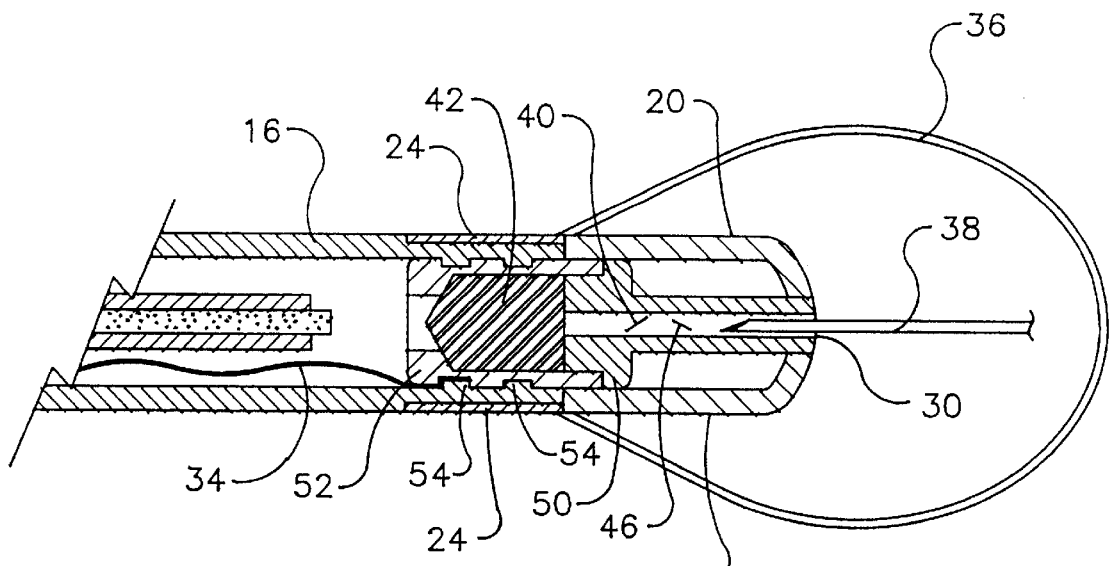
FIG. 4 is a detailed view of the proximal end of the infuser shown in FIG. 3.

The present invention includes a unique intravesical infuser device suitable for delivery into a body cavity such as the bladder. The device can be filled with a substance, which results in a reversible shape change to prevent voiding of the filled device or obstruction of the bladder neck. The device provides controlled site specific delivery of the drug into the bladder over an extended period of time.

With reference to FIG. 1, the infuser 10 has a proximal end 12 and a distal end 14. In general, for the infuser 10 to be appropriate for use in a human bladder, the uninflated length of the infuser 10 should be about 4 inches and may be in a range of about 3 to 6 inches long. The uninflated diameter of the infuser 10 should be about 0.25 inches. Extending between the proximal end 12 and the distal end 14, in one preferred embodiment, is an elastomeric pressure member 16 suitable for containing and pressurizing a liquid or fluid drug. The elastomeric pressure member 16 may be made of any suitable elastic medical grade polymer and is preferably made of medical grade dimethyl siloxane (silicone). For example, the elastomeric pressure member 16 may be USP class VI silicone tubing, 60+/−10 Shore A with a peroxide cure, having approximately a 3/16 inch inner diameter and approximately a 1/4 inch outer diameter. The elastomeric pressure member 16 can also be made of other elastic materials such as coated or uncoated polyurethanes, polystyrenes, butyl rubbers, latex rubber or other natural or synthetic elastomers. The elastomeric pressure member 16 may be about half an inch shorter than the infuser 10. A proximal end cap 20 may be provided at the proximal end 12. The proximal end cap 20 may be about 0.44 inches long and about 0.25 inches in diameter.

A distal end cap 22 is similarly provided at the distal end 14 of the infuser 10. The distal end cap 22 is about 0.57 inches long and 0.25 inches in diameter.

A proximal collar 24 may be used to secure the pressure member 16 to the proximal end cap 20. Similarly, a distal collar 26 may be used to secure the pressure member 16 to the distal end cap 22 of the infuser 10. The proximal end cap 20, proximal collar 24, distal end cap 22, and distal collar 26 may be formed of any relatively rigid thermoplastic polymer, having long-term biocompatibility in vivo, such as G. E. Ultem 1000 from General Electric of Pittsfield, Mass. The infuser 10 may be assembled using a variety of adhesive compounds, such as an epoxy.

A proximal opening 30 is provided at the proximal end 12 of the infuser 10, for introduction of fluid into the pressure member 16. The diameter of the proximal opening 30 may be about 0.1 inches. A distal opening 32 is provided at the distal end 14 of the infuser 10, through which drug pressurized by the pressure member 16 exits the infuser 10 at a controlled rate. The diameter of the distal opening 32 may be about 0.07 inches. Of course, modifications and adaptations of the device are contemplated wherein both openings 30, 32 are at one end, or wherein one opening serves for the purpose of filling, delivery and purging.

FIG. 2 illustrates the infuser 10 in its filled or inflated state. Whereas the empty infuser of FIG. 1 is relatively straight in profile and the pressure member 16 may be somewhat flaccid, the filled infuser 10 illustrated in FIG. 2 is stretched causing the pressure member 16 to be relatively rigid. The embodiment illustrated in FIG. 2 includes a tensile member 34 connecting the proximal end 12 and the distal end 14. The tensile member 34 may be made from a variety of generally inextensible materials, including wire, fabric or polymer. For example, the tensile member 34 can be a polyester ribbon approximately 0.006 inches thick by 0.085 inches wide as supplied Berwick industries, Inc. of Berwick, Pa. When the pressure member 16 is inflated or filled with a substance, the tendency is for the pressure member to extend both radially and axially. However, axial extension is inhibited by the tensile member 34. As a result, the infuser assumes a non-linear profile. In the embodiment illustrated in FIG. 2, the infuser 10 assumes a crescent or annular shape as a result of the tension induced by the tensile member 34.

When the device is used as an intravesical infuser 10, the non-linear shape may advantageously inhibit undesirable spontaneous or accidental voiding of the filled or inflated infuser 10. In general, for the infuser 10 to be appropriate for use in a human bladder, the inflated volume of the infuser 10 may be about 30 cc to about 40 cc. However, in some cases, it may be advantageous to increase the inflated volume above 60 cc or decrease it below 10 cc. Although the shape illustrated in FIG. 2 is a crescent, it will be understood that other shapes, including sinusoidal, helical, supercoiled, and random folded shapes are also within the scope of the present invention. From another perspective, it should be understood that the shape change that prevents accidental voiding of the device is a change in profile. Thus, if the device when implanted has a cylindrical shape with a diameter of 6 mm, for example, allowing it to readily traverse the urethra, it may well have a crescent shape with a annular diameter of 150 mm, 200 mm, or more when filled in the bladder. This change in profile itself can reduce the chance of accidental voiding.

One feature of the shape-changing is that a first shape facilitates the placement of the infuser in the bladder through the urethra and a second shape prevents spontaneous voiding of the infuser. Preferably, the second shape also facilitates micturition by retaining a shape which does not occlude the bladder neck. For example, in the embodiment described above, the cylindrical first shape has-a diameter that is less than the diameter of the urethra so that it may be placed into the bladder through the urethra. Once inserted, the infuser in the annular second shape does not pass out the urethra nor does it block the bladder neck and prevent the patient from micturating.

As the contents of the device are dispensed into the bladder, the device may experience at least a partial shape change reversal. The shape change reversal may facilitate removal of the device. In one embodiment, the device has shape memory so that the device does not return to its original shape simply by dispensing its contents. In this way, even after dispensing some or all of the contents of the device, the device retains a shape which does not pass out the urethra or block the bladder neck.

FIG. 3 illustrates the infuser 10 in longitudinal cross-section in a flaccid state. The infuser 10 illustrated in FIG. 3 includes an optional capture member 36 at both the proximal end 12 and distal end 14 of the infuser 10. The capture member 36 may be a loop of suture material such as suture 2-0, thermoplastic polymer, silicone, polytetrafluoroethylene, or any other suitable biocompatible material. Although a loop configuration is illustrated, any other suitable configuration capable of being attached or grasped by a retrieval device may be used. Such configurations would include molded handles or latching mechanisms in the infuser device 10 itself.

As seen in more detail in FIG. 4, the proximal end cap 20 is adapted to receive a hypodermic needle 38. The hypodermic needle 38 inserted into the proximal opening 30 can extend through a guide channel 40 to encounter a valving member 42. In the illustrated embodiment, the valving member 42 is a septum seal. The valving member 42, when configured as a septum, is preferably made of silicone, rubber or other biocompatible elastomeric or viscous material. For example, the valving member 42 may be made of a 2-part silicon potting compound supplied by A. E. Yale Enterprises of San Diego, Calif. under the part numbers VSI 1065A and VSI HI PRO GREEN. The valving member 42 may be about 0.25 inches long and 0.161 inches in diameter. Septum seals, such as the valving member 42, may be pierced one or more times to allow access to the interior of a vessel, while resealing after the piercing device is removed. In the present invention, the combination of the guide channel 40 and the septum seal 42 tend to retain the infuser 10 firmly attached to the hypodermic needle 38 during introduction of the infuser 10 into the bladder. Still with reference to FIG. 4, the proximal end cap 20 may advantageously comprise an outer shell 44 that is generally cup-shaped. A smaller needle port 46 fits concentrically inside the outer shell 44. The needle port is tube-shaped with a small proximal end extending to the proximal opening 30 and defining the guide channel 40 as the needle port 46 extends in a distal-direction. An annular flange 50 extending radially outwardly from the guide channel 40 attaches the needle port 46 to the interior of the outer shell 44. Thus, the needle port 46 surrounding the guide channel 40 is glued, ultrasonically welded, or otherwise suitably attached to the outer shell 44 at the proximal opening 30 and is also attached by means of the flange 50 to the distal portion of the outer shell 44. The embodiment of the proximal end cap 20 illustrated in FIG. 4 further includes a septum retainer 52 sitting concentrically inside the distal end of the outer shell 44 and extending distally therefrom. The proximal end of the septum retainer 52 abuts against the annular flange 50. The distal end of the septum retainer 52 extends distally from the outer shell 44, coaxially with the outer shell 44. In one preferred embodiment, the septum retainer 52 includes ridges or grooves 54 for retaining the pressure member 16 securely with the proximal end cap 20. The inner diameter of the annular septum retainer 52 narrows at the distal end thereof. When assembled into the outer shell 44 to abut the flange 50, the septum retainer 52 compresses the septum 42 against the flange 50 at the proximal end of the septum 42 and against the narrowed portion of the septum retainer 52 at the distal end thereof.

The pressure member 16, which is preferably in the form of a tube, is slid over the outside of the distal portion of the septum retainer 52. It is then locked in place on the proximal end cap by the proximal collar 24 that traps the pressure member 16 tightly between the septum retainer 52 and the proximal collar 24, providing a leak-proof seal. Retention of the pressure member 16 under pressure is facilitated by the ridges or grooves 54 on the septum retainer 52. The proximal collar 24 may advantageously further secure the capture loop 36 by capturing the ends of the capture loop 36 under the proximal collar 24. Similarly, the pressure exerted radially inwardly by the proximal collar 24 can be used to secure a tensile member 34. The tensile member 34 is preferably trapped between the pressure member 16 and the septum retainer 52 by the pressure exerted by the proximal collar 24 on the proximal end of the pressure member 16.

With reference again to FIG. 3, the distal end 14 of the infuser 10 provides controlled release of the drug from the pressure member 16 by means of the distal opening 32. In the illustrated embodiment, a linear resistor 56 is provided to control the flow of fluid from the interior of the pressure member 16 through the distal opening 32. In early prototype versions of the infuser 10, the linear resistor 56 comprises a small cotton string, suture or other suitable resistor element 60 surrounded by an impervious coating 62. We have found that cotton crochet thread surrounded by heat-shrink polyolefin material makes a satisfactory linear resistor 56. One satisfactory cotton crochet thread is 4 strand white wound cotton fiber approximately 0.022 inch in diameter manufactured by Coats and Clark, Inc. of Greensville, S.C. under the part number Article C-44. A cotton crochet thread manufactured by Coats and Clark, Inc. of Greensville, S.C. under the trademark CROSHEEN can also be used. One satisfactory impervious coating 62 is heat shrink polyolefin with an expanded inner diameter of 0.032 inches supplied by Raychem, Menlo Park, Calif. The resistance generated by the linear resistor 56 is a function of its length, diameter and the materials from which it is constructed, and, for any given pressure, the flow rate for a particular linear resistor 56 can readily be determined by empirical methods. For example, the suitable resistor element 60 may be about 0.5 inches to 10 inches long. In the general case, it is typically advantageous if the infuser 10 flow rate remains constant within about +/−50%, preferably +/−30% or +/−20% over a variety of pressure conditions.

In one preferred embodiment of the invention, the end caps 20, 22 include air pockets 64 to provide buoyancy. Of course, as an alternative to the use of air pockets, the ends caps 20, 22 could instead be made of low density material or could include air bladders inside or outside the end caps 20, 22 or other suitable means for promoting buoyancy. By making the end caps 20, 22 lighter than the rest of the infuser 10, the caps 20, 22 will tend to float. Because the urethra is located in the bladder neck generally at the bottom of the bladder when a person is standing erect, the end caps 20, 22 will tend to float when the bladder fills and during micturition. This, in turn, presents the curved middle portion of the curved infuser 10 to the exit of the bladder. Because this curved portion extends generally transversely to the direction of flow, it is unlikely that the filled or inflated infuser 10 would be accidentally voided or would obstruct the bladder neck while the infuser 10 is in a curved or arcuate configuration with buoyant end caps. The buoyant end caps 20, 22, also help to minimize or prevent irritation of the trigone region and neck of the bladder, thereby minimizing patient discomfort.

Figure 5:
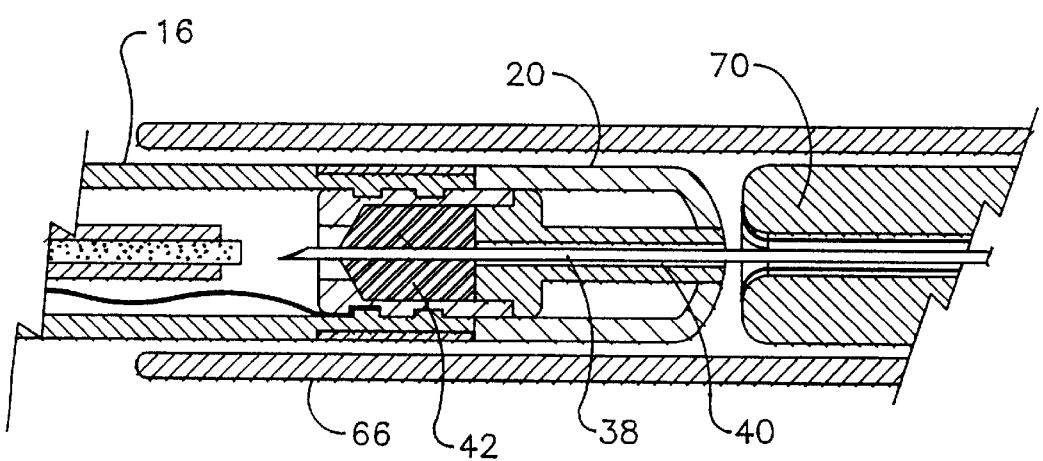
FIG. 5 is a longitudinal cross-section of the proximal end of the infuser of FIG. 3, in combination with an introducer device.

FIG. 5 schematically illustrates one method for introducing the infuser 10 into the bladder. An outer sheath 66 is provided into which the infuser 10 can fit concentrically when in the deflated or unfilled state. After transurethral introduction of the outer sheath 66 into the bladder, the deflated infuser 10 is passed through the outer sheath 66. Located concentrically within the outer sheath 66 is an extender 70 having a diameter approximately the same as that of the infuser 10. Finally, a hypodermic needle 38, positioned concentrically within the extender 70, is inserted into the septum 42 of the infuser 10 to retain the infuser 10 against the hypodermic needle 38 and prevent loss of the infuser 10 during inflation or filling. The hypodermic needle 38 is connected at its proximal end to a fluid source (such as a source of liquid drug) (not shown). With the outer sheath in place in the bladder, the extender 70 and hypodermic needle 38 are used to push the infuser 10 through the outer sheath 66 into the bladder. Fluid is then introduced through the hypodermic needle 38 to fill the pressure member 16 with fluid and to induce a change of shape of the infuser 10. After the infuser 10 is filled, the hypodermic needle 38 is disconnected from the infuser 10 and withdrawn through the extender 70, The infuser 10 is allowed to float freely within the bladder of the patient. The extender 70 and the outer sheath 66 are then withdrawn from the bladder of the patient.

FIG. 19 is a longitudinal cross-section of an alternate embodiment of the intravesical infuser in a flaccid state. The infuser 10 illustrated in FIG. 19 includes an optional capture member 236 at the distal end 14. The distal end 14 of the infuser 10 is also used for normal drug delivery and for draining of the drug, if necessary, during the removal process. The infuser 10 illustrated in FIG. 19 allows the introduction of fluid under pressure into the pressure member 16 through a check valve 242 at the proximal end 12. The check valve 242 prevents fluid from exiting the infuser through the proximal end 12 of the infuser 10 after the fluid has been introduced into the infuser 10. As shown in more detail below, the check valve 242 eliminates the need for the hypodermic needle 38 to puncture the valving member 42 as shown in FIGS. 4 and 5. The pressure valve 242 facilitates a more rapid filling of the infuser 10 by eliminating the flow resistance in the hypodermic needle 38.

Figure 20:
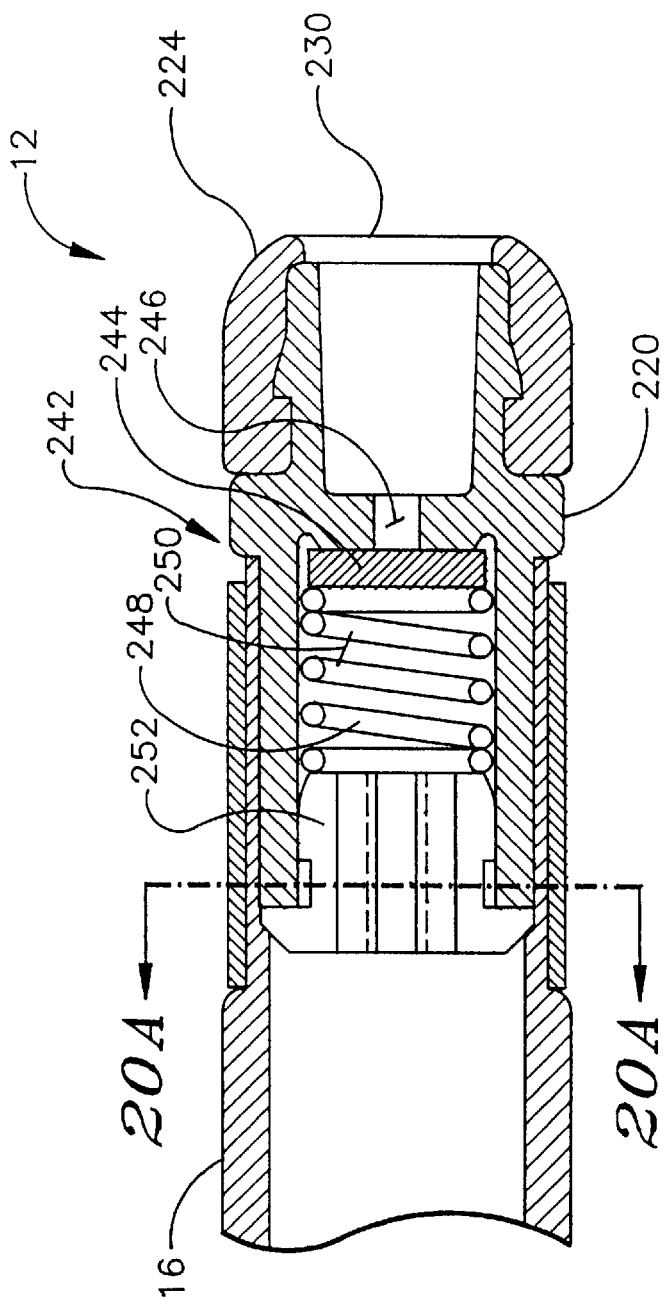
FIG. 20 is a detailed view of the proximal end of the infuser shown in FIG. 19.
Figure 20A:
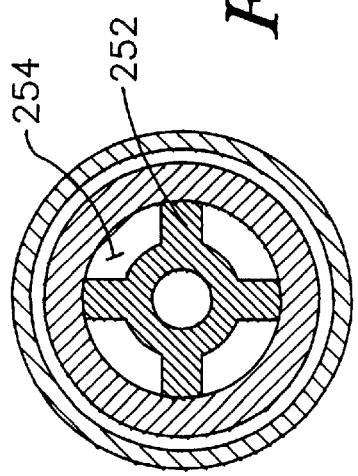
FIG. 20A is a cross-sectional view illustrating the grooves in the check valve retainer of FIG. 20.

The check valve 242 is shown in detail in FIG. 20. A proximal endcap form 220 is covered by an endcap bumper 224 that is more compliant and softer than the proximal endcap form 220. The use of the more compliant material on the endcap bumper 224 reduces the trauma caused by contact of the proximal end 12 with tissue. In one embodiment, the endcap bumper 224 is polymeric material. The proximal end 12 has an opening 230 which permits access to a check valve entrance 246. When ample fluid pressure presses upon a floating disc 244 at the distal end of the check valve entrance 246, the floating disc 244 is displaced and moves away from the valve entrance 246 allowing fluid to enter a fluid chamber 250. The fluid in the fluid chamber 250 enters the lumen of the pressure member 16 through grooves in a check valve retainer 252. FIG. 20A is a cross-sectional view illustrating more clearly four grooves 254 in the check valve retainer 252. Pressure generated by the pressure member 16 causes the floating disc 244 to occlude the check valve entrance 246 upon completion of fluid introduction. A small spring 248 maintains a pressure against the floating disc 244 to keep the check valve 242 closed even when the pressure within the fluid chamber 250 is approximately the same as the pressure within the opening 230.

The distal end 14 of the infuser 10 is shown in detail in FIG. 21. The distal end 14 incorporates the optional capture member 236. The capture member 236 may be made of similar material as described for the capture member 36 such as a 2–0 suture. It is advantageous to have the capture member 236 connected from the center of the distal end 14 so that the infuser 10 aligns itself with a pulling force applied to the capture member 236. The distal end 14 also incorporates a flow restrictor 256 that meters the flow of fluid from the pressure member 16 through a distal opening 232. The flow restrictor 256 can be made from a variety of sintered or porous metal or polymer materials. For example, the flow restrictor 256 can be a 0.062 inch diameter, 0.06 inch long cylinder of sintered titanium with a pore size of 0.1 microns as manufactured and supplied by Mott Corporation of Farmington, Conn. or stacked porous polycarbonate membrane discs 13 mm in diameter with a pore sizes of 0.01 or 0.05 microns manufactured and supplied by Osmonics of Livermore, Calif., as catalog numbers 10505 and 10501, respectively.

The flow restrictor 256 is contained within a flow restrictor housing 280. The flow restrictor housing 280 is contained within a distal endcap form 222 by a valve seat 226. The valve seat 226 seals an interior lumen of the distal endcap form 222 constraining fluid in the pressure member 16 to flow through a valve seat flow channel 282. An o-ring 286 seals the valve seat 226 to the flow restrictor housing 280 constraining the fluid to flow through the flow restrictor 256 and not around the flow restrictor housing 280. A flow restrictor housing spring 284 presses on the flow restrictor housing 280 forcing it against the valve seat 226 placing pressure on the o-ring 286 maintaining the integrity of the seal between the valve seat 226 and the flow restrictor housing 280. The distal endcap form 222 is covered by a distal endcap bumper 228. The distal endcap bumper 228 is made of a compliant material which reduces the trauma caused by contact of the distal end 14 with tissue.

On the outlet side of the flow restrictor 256, a retainer 288 holds the capture member 236. The capture member 236 exits the infuser 10 through the distal opening 232. The positioning of the capture member 236 facilitates the removal of the infuser 10 by allowing the device to pulled out of the bladder through the urethra. If the capture member 236 is pulled while sufficient opposite pressure is maintained against the distal endcap bumper 228, the flow restrictor housing spring 284 compresses thus releasing the pressure on the o-ring 286. In this way, fluid within the pressure member 16 may flow around the flow resistor housing 280. This configuration facilitates the rapid purging of the fluid contents of the pressure member 16 which decreases the profile of the infuser 10 thus facilitating the removal of the device.

Figure 26:
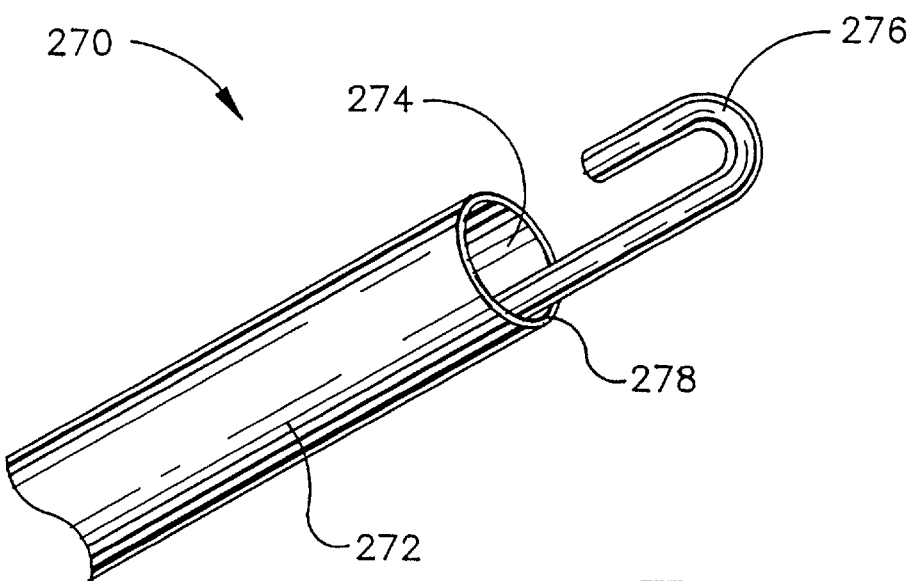
FIG. 26 illustrates a retrieval device which might be used to retrieve the infuser illustrated in FIG. 19 from the patient

FIG. 26 illustrates a retrieval device 270 which might be used to retrieve the infuser 10 from the patient. A capturing element 276 is retractably disposed within a retrieval channel 274. To remove the infuser 10, a sheath 272 is introduced into the bladder. Once introduced, the capturing element 276 is extended into the bladder and engages the capture member 236. The capturing element 276 is retracted into the retrieval channel 274 drawing the distal endcap bumper 228 into a sealed fit with a channel entrance 278. The compliant material used to form the distal endcap bumper 228 facilitates sealing between the distal end 14 and the channel entrance 278. As the pressure against the infuser 10 increases, the flow restrictor housing spring 284 compresses thus releasing the pressure on the o-ring 286 and creating a fluid path from within the elastomeric pressure member 16 to the retrieval channel 274. In this way, any remaining fluid within the infuser 10 may be purged from the infuser 10 to lower the profile of the infuser 10 for extraction through the urethra while avoiding the introduction of the fluid into the bladder.

Figure 22:
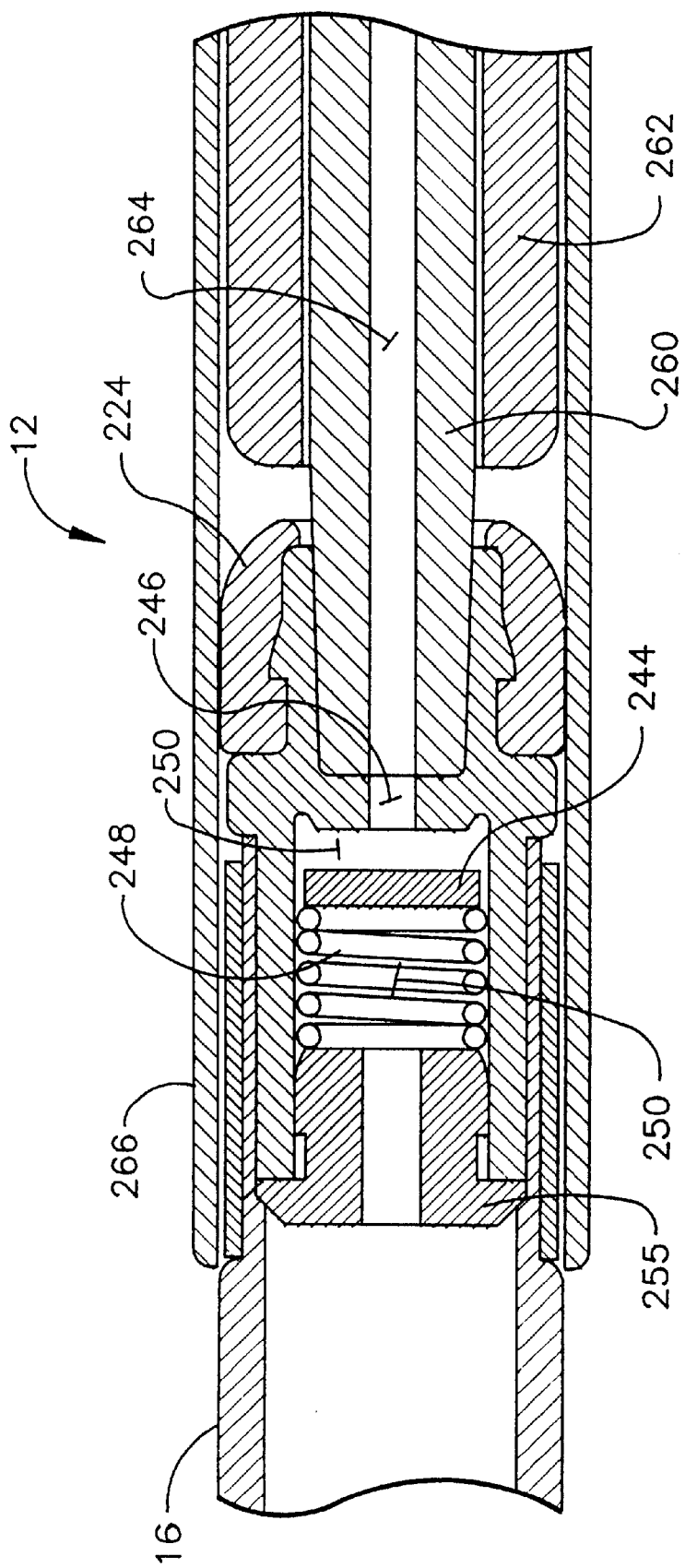
FIG. 22 is a longitudinal cross-section of the proximal end of the infuser of FIG. 19, in combination with an introducer device.

FIG. 22 is a longitudinal cross-section of the proximal end of the infuser 10 of FIG. 19, in combination with an introducer device. An outer sheath 266 is provided into which the infuser 10 can fit concentrically when in the deflated or unfilled state. After transurethral introduction of the outer sheath 266 into the bladder, the deflated infuser 10 is passed through the outer sheath 266 into the position shown in FIG. 22. Located concentrically within the outer sheath 66 is an extender 262 having a diameter approximately the same as that of the endcap bumper 224. At the distal end of the extender 262 is a secure coupling fitting 260 that fits snugly into the opening 230 of the infuser 10. For example, the secure coupling fitting 260 may be a luer fitting. The snug fit of the secure coupling fitting 260 into the opening 230 of the infuser 10 prevents loss of fluid during filling or inflation. An introducer channel 264 located within the extender 262 provides a fluid path for a fluid source (not shown) connected at the proximal end of the extender 262. Pressurized fluid from the fluid source compresses the small spring 248 and displaces the floating disc 244 away from the valve entrance 246. Fluid flows from the introducer channel 264 through the valve entrance 246, into the fluid chamber 250 and fills or inflates the infuser 10. When filling is complete, the fluid pressure in the introducer channel 264 is reduced and the floating disc 244 returns to its original position occluding the valve entrance 246. The secure coupling fitting 260 is disconnected from the infuser 10 and retracted into the extender 262. The retraction of the extender 262 releases the infuser 10 to free float in the bladder of the patient. The outer sheath 266 and extender 262 assembly are then withdrawn from the patient.

In preferred embodiments of the invention, it is advantageous to provide a pressure-responsive valve assembly to control the flow of drug out of the pressure member 16 of the infuser 10. Because the pressure profile of an elastomeric pressure member infuser decreases over time, as the volume of drug (and thus the pressure) inside the pressure member decreases, a linear resistor such as element 56 in FIG. 3 provides a time-variable flow. It is more advantageous to provide a relatively constant rate of drug delivery to the bladder. This can be accomplished, in a preferred embodiment, by pressure-responsive valving, as illustrated in FIG. 3A.

In FIG. 3A, the infuser 10 is generally as described in connection with FIG. 3, wherein like reference numerals reflect like parts. However, toward the distal end 14 of the infuser 10, a pressure-responsive valve 74 utilizing movable walls 86 to reduce the area of a flow channel 76 is used to control the flow of fluid out of the infuser. Appropriate valving mechanisms are described in more detail in connection with FIGS. 6–12, and any of the described valves could be adapted for use in the invention.

The operation of one suitable type of pressure-responsive valve is illustrated in FIG. 6. A pressure source P1 directs fluid from a fluid reservoir 72 into a valve assembly 74 through a flow channel 76. When the fluid reaches the valve assembly 74, the valve assembly 74 is subjected to an exterior and interior pressure differential that creates a flow resistance proportional to the differential pressure in question. Thus, with reference to FIG. 6, the exemplary pressure P1 in the fluid reservoir 72 is also applied to the exterior of the valve assembly 74. This pressure P1 reduces the flow area of the portion of the flow of channel 76 extending through the valve assembly 74 or otherwise increases resistance to flow through the flow channel 76, dropping the pressure in the flow channel 76 to a lower pressure P3 as it exits the valve assembly 74. The fluid continues along the flow channel 76 to the exit 80. In a preferred embodiment, a linear resistor 82 is provided between the fluid reservoir 72 and the valve assembly 74 within the flow channel 76. The linear resistor 82 may be of the construction detailed in FIG. 3, or, alternatively, may be of any other desired construction, such as a serpentine path, capillary tubing or a series of collateral passages. As seen in FIG. 6, after the fluid passes through the linear resistor 82, the pressure P1 entering the linear resistor 82 has been reduced to a lower pressure P2. In that manner, when the pressure P1 is exerted on the valve assembly 74 (e.g., on the outside of the valve assembly 74), the ability of the pressure P1 to constrict the flow channel 76 within the valve assembly 74 will not be counteracted by the pressure P2 as effectively as if the pressure in the valve assembly 74 had been P1. Thus, by reducing the pressure inside the valve assembly 74, the linear resistor 82 facilitates effective restriction of fluid flow by the valve assembly 74.

Note that in this type of pressure-responsive valving, fluid flow can be maintained relatively constant despite variations in the pressure of the fluid reservoir. That is because higher pressures (which would ordinarily facilitate greater flow) are counteracted by greater constriction of the flow channel 76 through the valve assembly 74. Conversely, as the pressure P1 in the fluid reservoir 72 decreases, the flow channel 76 through the valve assembly 74 is increased in size or cross-sectional area, thus compensating for the reduced pressure driving fluid through the flow channel 76.

In another preferred embodiment, a second resistor element, exit resistor 84, is provided between the valve assembly 74 and the exit 80. The exit resistor 84 can protect against transient pressure spikes (such as those induced by coughing or other increases in abdominal pressure). Such pressure spikes, in the absence of exit resistor 84, could send pressure backwards through the exit 80, opening up the flow channel 76 through the valve assembly 74, and resulting in possible release of a bolus dosage or spike.

Figure 7:
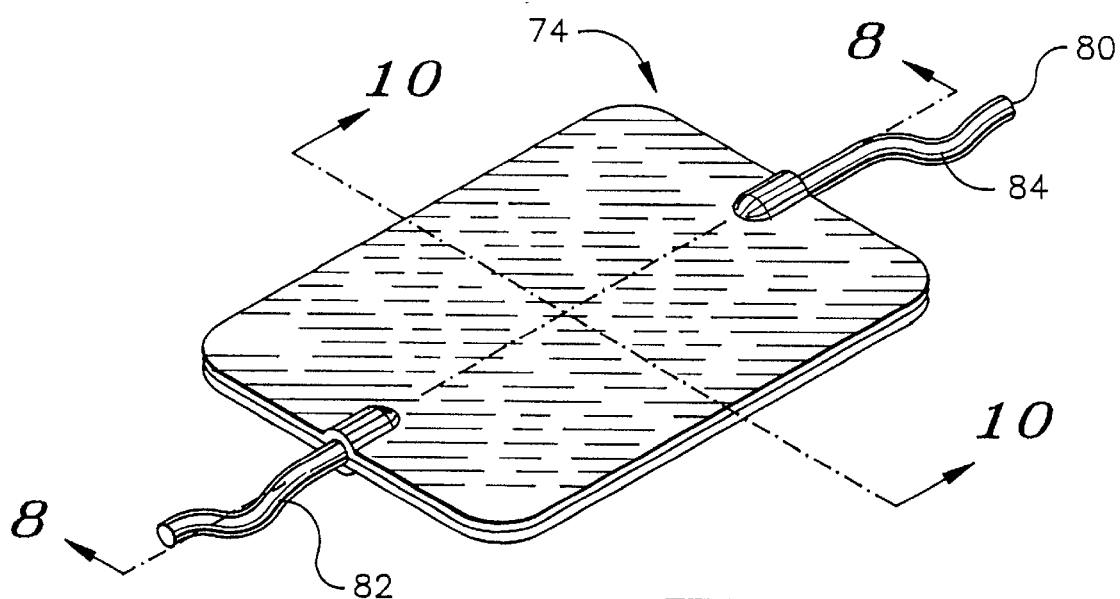
FIG. 7 is a perspective view of a pressure-responsive valve for use in the present invention.

One embodiment of a valve assembly 74 is shown in FIG. 7. In this embodiment, a linear resistor 82 directs fluid into a first end of the valve assembly 74. An exit resistor 84 directs fluid out of the exit 80 and into the patient. The valve assembly 74 is preferably located within the pressure member 16 of the infuser 10. The valve assembly 74 can also be located outside of the pressure member 16 of the infuser 10 in fluid communication with the interior of the pressure member 16 of the infuser 10.

A longitudinal cross-section of the valve assembly 74 is schematically illustrated in FIGS. 8 and 9. FIG. 8 illustrates a linear resistor 82 comprising a resistor element 60 covered by an outer sheath 66 on the upstream end of the valve assembly 74. A flow channel 76 extends through the valve assembly 74 leading to an exit resistor 84, also having a resistor element 60 surrounded by an outer sheath 66. The flow channel 76 through the valve assembly 74 is defined by one or more movable walls 86. The movable walls 86 may be formed of any deformable material, preferably in the form of a sheet or a web, such as polyethylene, teflon, polyvinyl chloride, polytetraflouorethylene, polyvinylidine chloride, thin stainless steel and the like.

As shown in FIG. 9, when an external pressure (indicated by arrows P) impinges on the exterior of the movable walls 86, the movable walls are pressed inwardly into the flow channel 76, constricting the flow channel 76. In this manner, as the pressure P increases, the cross-sectional area of the flow channel 76 decreases, thereby constricting the flow of fluid through the valve assembly 74. It will be appreciated that a wide variety of configurations and materials can be used to construct movable walls that will compress against a flow channel upon the application of pressure to the movable wall. Any such pressure-responsive valve utilizing a movable wall, or other pressure-responsive elements, such as those in which the flow pressure acts against a spring or the like, are considered to fall within the scope of the present invention.

Figure 10:
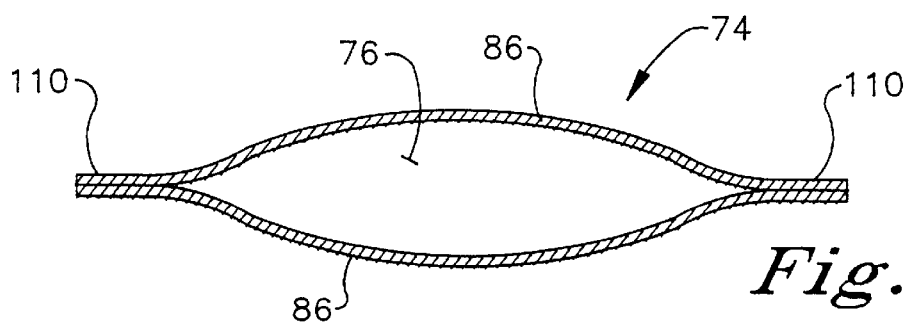
FIG. 10 is a transverse cross-section of one embodiment of the pressure-responsive valve illustrated in FIG. 7, taken along the line 10—10 in FIG. 7.
Figure 11:
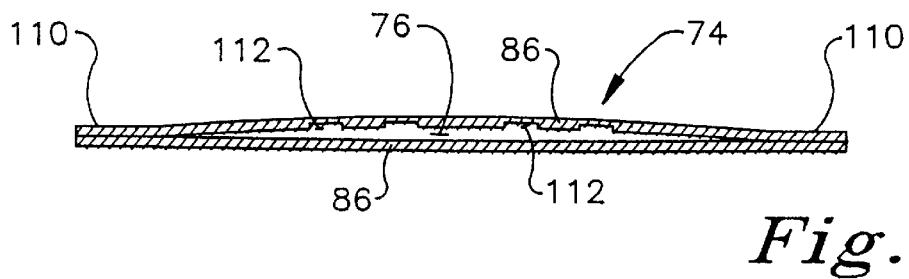
FIG. 11 is a transverse cross-section as in FIG. 10, illustrating an embodiment having minimum flow channels.
Figure 12:
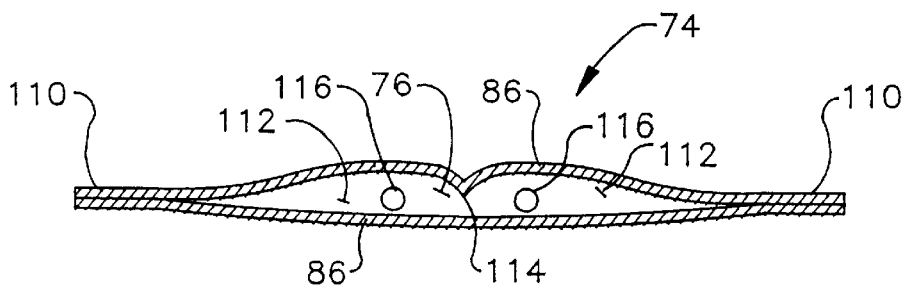
FIG. 12 is a transverse cross-section as in FIG. 10, illustrating an alternative flow channel embodiment.

FIGS. 10–12 illustrate certain suitable embodiments of the valve assembly 74, taken in transverse cross-section to the direction of the flow channel 76. FIG. 10 illustrates a simple valve assembly 74, featuring at least one movable wall 86 against a flow channel 76. In FIG. 10, the flow channel 76 is defined by two sheets of flexible polymer sealed at their edges 110 by any suitable means, such as heat sealing, solvent welding, RF welding, crimping, clamping, and the like.

FIG. 11 is an embodiment similar to that illustrated in FIG. 10, except that the movable walls 86 or a surface against which the movable wall 86 is placed is provided with minimum flow channels 112, such as longitudinal grooves, ridges, or the like, to provide at least a minimum flow channel through the valve 74 despite the pressure exerted against the movable wall 86. The minimum flow channels 112 prevent the movable walls 86 from sticking together under high external pressure and reducing the flow channel 76 to an unacceptably small area. The length, height, and width of the flow channels 112 effects the area of the flow channel 76 and thus can be chosen to achieve desired flow characteristics of the valve assembly 74.

A similar arrangement is illustrated in FIG. 12, in which the patency of the flow channel 76 is maintained by a permanently formed ridge 114 between two longitudinally extending flow channels 112. High external pressure would force the movable walls 86 close together, but the curvature of the interior of the movable wall 86 (or a ridged surface against which is presses) would tended to keep at least a small flow channel 76 open under any normal operating pressure. In addition to the minimum flow channels 112 or ridges 114, one may advantageously provide wicking elements 116, as illustrated in FIG. 12, for maintaining the flow channel 76 open or for providing a minimum flow channel in the event of a relatively high external pressure. In FIG. 12, the wicking elements 116 are pictured as having a circular cross-sectional area. In other embodiments, the wicking elements may have a rectangular cross-sectional area or any other desired shape. Alternatively, the wicking elements may be comprised of webbing or a web of flat material. In a similar manner as described above, the length and diameter of the wicks 116 effect the area of the flow channel 76 and thus can be chosen to achieve desired flow characteristics of the valve assembly 74.

Figure 23A:
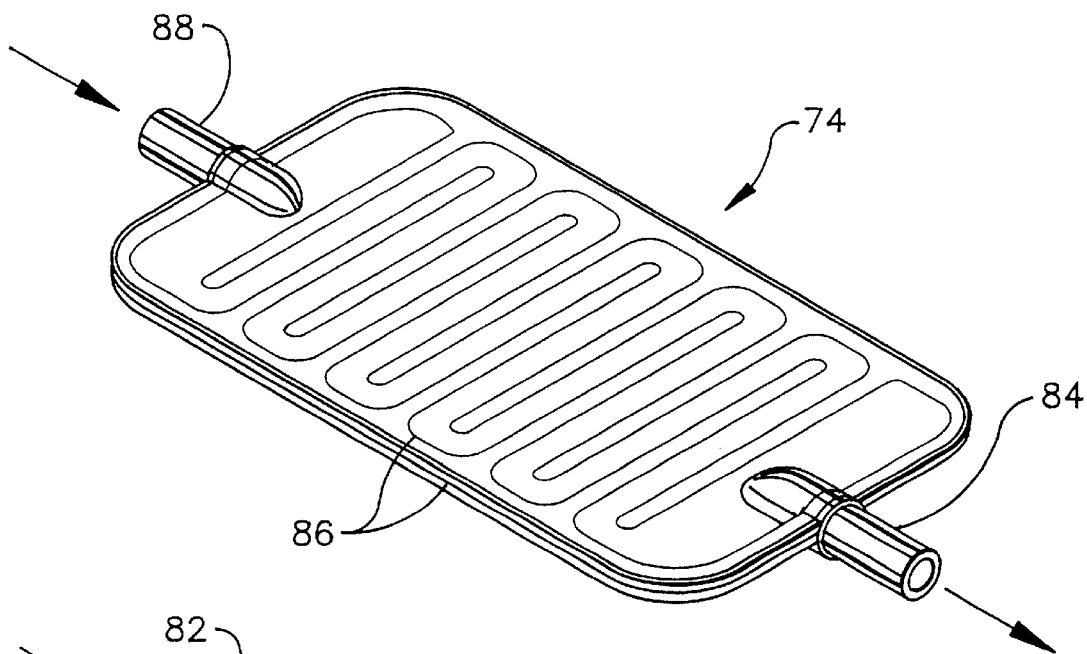
FIGS. 23A–B are a perspective and a cut away view of an alternative pressure-responsive valve for use in the present invention, respectively.
Figure 23B:
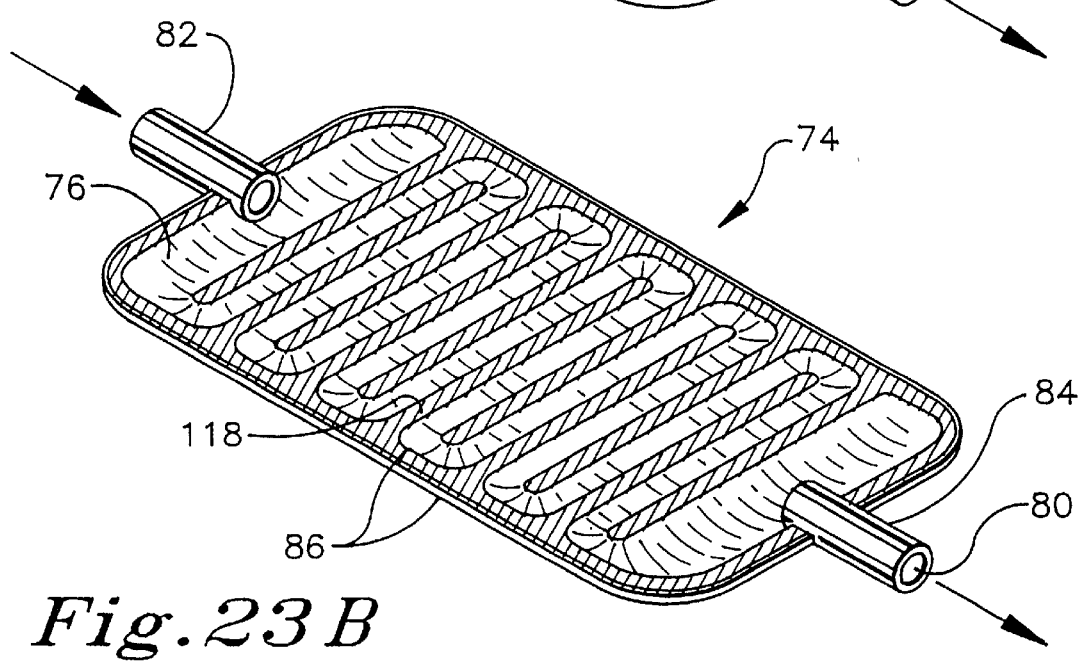

An alternate embodiment of a pressure-responsive valve 74 is shown in FIGS. 23A–B. A tortuous flow channel 76 is created by bonding the movable walls 86 to form flow barriers 118. The fluid is constrained to flow around the flow barriers 118 to reach the exit resistor 84 and exit the valve assembly 74. The movable walls may be bonded using any method for bonding thermoplastics such as heat sealing, ultrasound welding, and solvent bonding. The number and width of the flow barriers 118 determines the degree of constriction of the flow channel 76 by the external pressure acting on the valve assembly 74. Increasing the width or number of flow barriers 118 acts to reduce the flow through the flow channel 76 at the same pressure.

Figure 24:
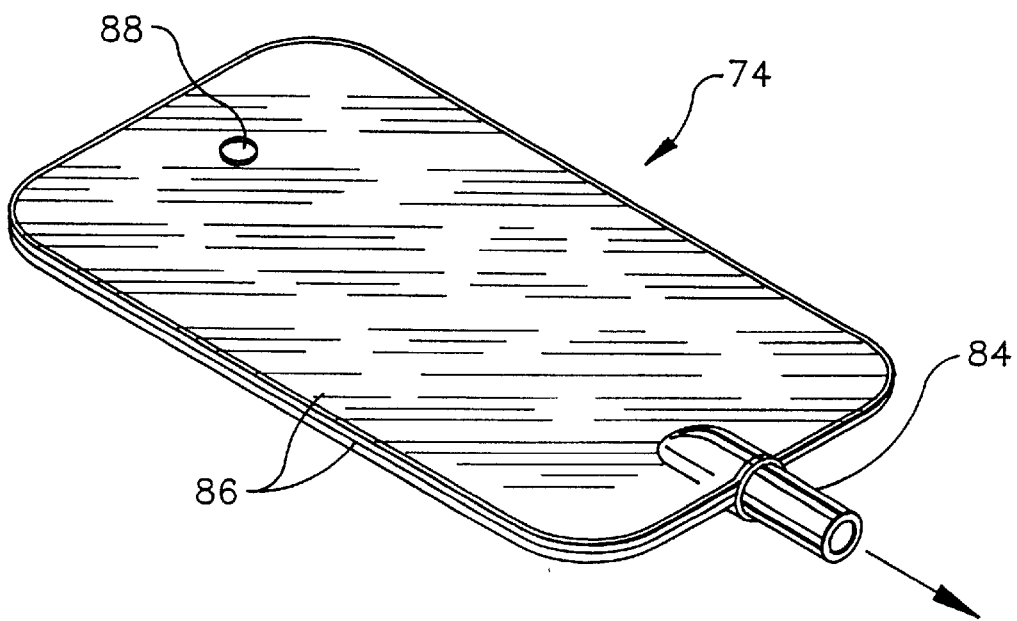
FIG. 24 is a perspective view of another alternative pressure-responsive valve for use in the present invention.

The design in FIG. 24 displays yet another method for creating a pressure-responsive valve. The valve assembly 74 of FIG. 24 has no linear resistor 82 as shown in FIG. 7. Instead, an opening 88 is located proximally in one movable wall 86 and provides the entrance for fluid into the valve assembly 74. The exit resistor 84 is located distal of the opening 88. The diameter of the opening 88 and the spacing between the opening 88 and the exit resistor 84 effects the amount of fluid leaving the valve 74. As the external pressure acting on the valve 74 decreases, the diameter of the opening 88 increases, the flow through the valve 74 increases. The distance between the opening 88 and the exit resistor 84 effects the area of the flow channel 76 and thus can be chosen to achieve desired flow characteristics the valve assembly 74.

In all the above described embodiments of the valve assembly 74, mechanical means were described to effect the flow characteristics of the flow channel 76. In addition, material properties of the movable walls 86 can be varied to effect the degree of compression caused by the external pressure. For example, high durometer polymers compress less and are, therefore, less effected by changes in pressure than low durometer polymers. Thus, a low durometer polymer provides a greater reduction of flow at high pressure by greater compression of the flow channel 76 and, therefore, provides a greater range of resistance for a given range of pressures than a high durometer material.

Figure 17A:
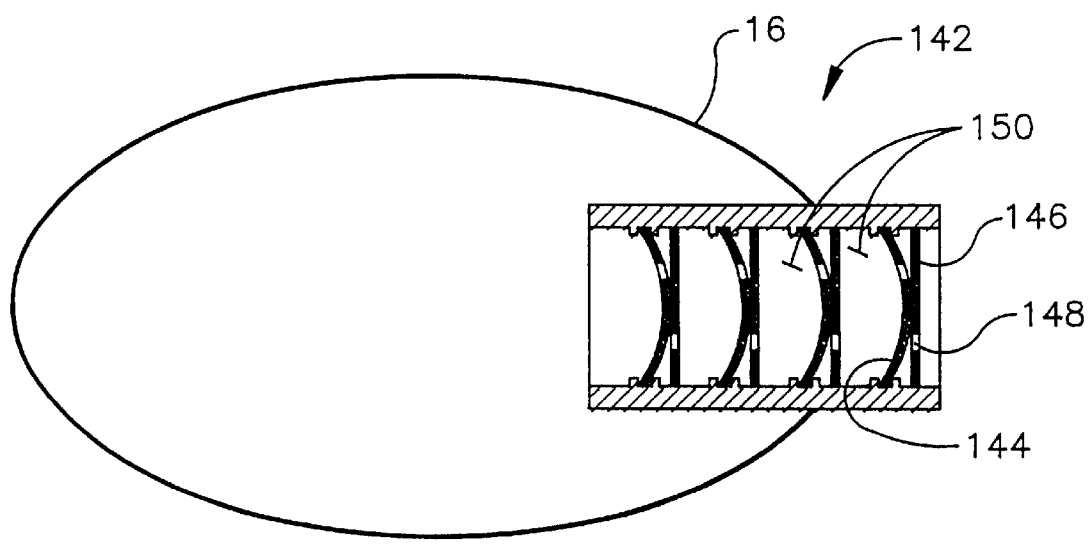
FIG. 17A is a transverse cross-section of a valve assembly of the type illustrated in FIG. 7, taken along the line 10—10, in which the valve assembly comprises compressible disks.
Figure 17B:
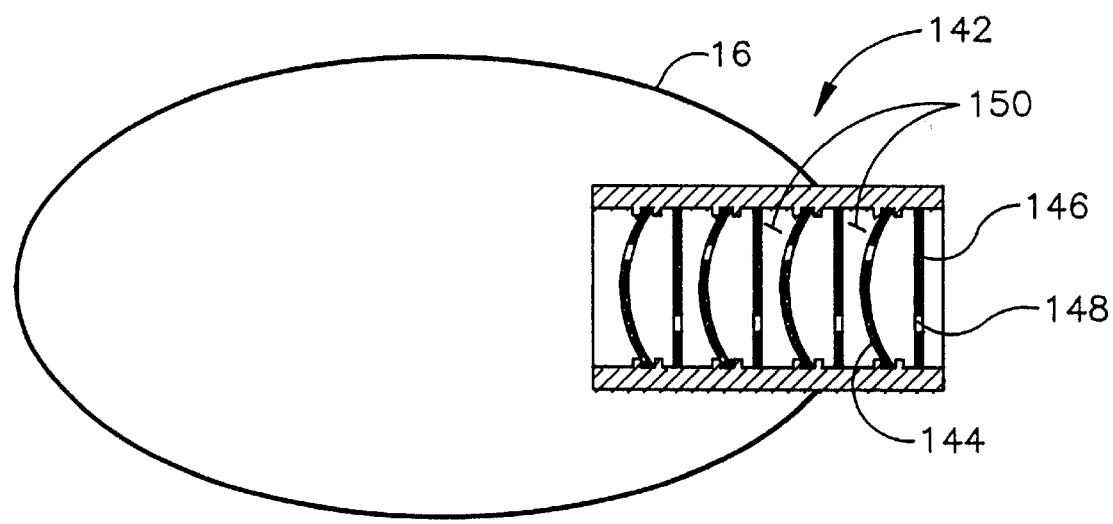
FIG. 17B corresponds to FIG. 17A, illustrating the opening of the flow channels as pressure drops in the infuser.

FIGS. 17A and 17B illustrate an alternative pressure-responsive valve assembly 142 which operates according to the principles just described. FIG. 17A is a cross-section of the valve 142 when the pressure in the pressure member 16 is relatively high. The high pressure causes a compressible disc 144 to deform and press against a flow plate 146. The compressible disc 144 may be made of any suitable pliable material such as polystyrene. Varying the physical properties or shape of the discs provides a method for effecting the compressibility of the compressible disc 114 and thus can be used to achieve desired flow characteristics of the valve assembly 74. When pressure is applied, the compressible disc 144 provides a partial occlusion of the flow channels 148. The partial occlusion acts as a resistance to flow. In this way, the pressure in each successive valve chamber 150 is less than the preceding chamber. The number of chambers which are used depends upon the desired flow rate, the pressure range within the pressure member 16 and the patient's bladder, the dimensions of the valve 142 and the dimensions and material properties of the compressible disc 144. FIG. 17B is a cross-section of the valve 142 when the pressure within the pressure member 16 has decreased below that shown in FIG. 17A. Note that the compressible disc 144 is no longer pressing against the flow plate 146 and flow resistance through the flow channels 148 has decreased.

Figure 18:
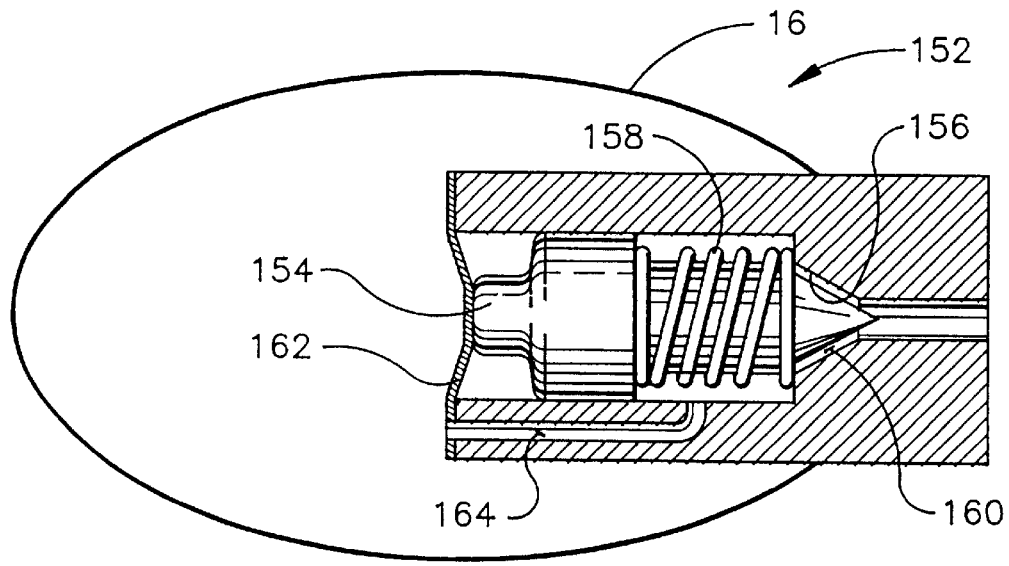
FIG. 18A illustrates a needle and seat valve assembly with constricted flow under high pressure.
FIG. 18B illustrates the needle valve of FIG. 18A, with an expanded flow channel under reduced infuser pressure.
Figure 18:
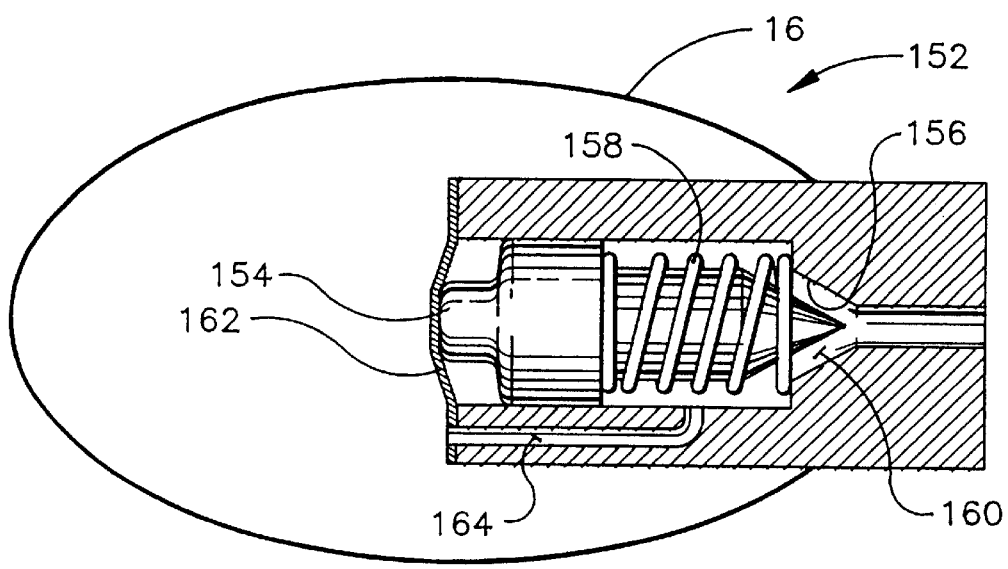

FIGS. 18A and 18B illustrate yet another pressure-responsive valve assembly 152. FIG. 18A is a cross-section of the valve 152 when the pressure in the pressure member 16 is relatively high. The high pressure causes a needle 154 to press towards a mated seat 156 thereby deforming a spring 158. In this position, the needle 154 provides a partial occlusion of a flow channel 160 between the needle 154 and the seat 156. The pressure member 16 and the needle 154 are isolated by a flexible membrane 162, although other embodiments may incorporate an o-ring between the needle 154 and the seat 156 to prevent fluid in the pressure member 16 to enter the flow channel 160. A fluid channel 164 provides a path for fluid to flow from within the pressure member 16 to the flow channel 160. The difference in pressure at the entrance and the exit of fluid channel 164 determines the degree of occlusion of the flow channel 160. Decreasing pressure within the pressure member 16 decreases the driving force through the fluid channel 164. FIG. 18B is a cross-section of the valve 152 when pressure within the pressure member 16 has decreased below that shown in FIG. 18A. Note that the spring 158 presses the needle 154 toward the flexible mebrane 162 and away from the seat 156, decreasing the resistance to flow through the channel 160.

Figure 13A:
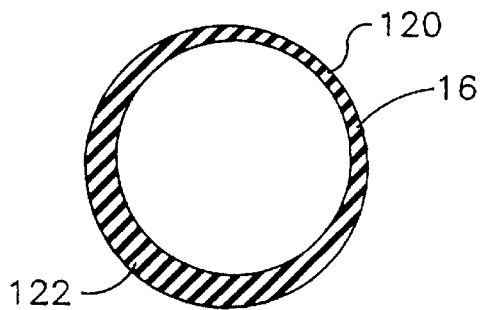
FIG. 13A illustrates one alternative embodiment of the pressure member of the infuser device, in a cross-sectional view taken along the line 13—13 FIG. 1.

The embodiments of the infuser illustrated in FIGS. 2 and 3 include a fabric tensile member 34 in the interior the pressure member 16. However, it should be appreciated that the term tensile member is interpreted broadly in the present invention. Multiple embodiments of the tensile member are illustrated in FIGS. 13A–13E. FIG. 13A is a cross-section of the pressure member 16 in the infuser 10 having a thin side 120 and a thick side 122. Because the thick wall 122 is less extensible than the thin wall 120, the infuser 10 will form into an arcuate, curved, or circular shape upon inflation. Note that the thick wall 122 can be a gradual thickening of the device, or alternatively, can be a ridge or stripe of thickened material. If the thick wall 122 runs along the same side of the pressure member 16 for its entire length, the two ends 12, 14 of the infuser 10 will curve toward each other. Alternatively, if the thick wall 122 spirals around the pressure member 16 along its length, the infuser will tend to assume a helical or spiral structure. Alternating the location of the thick wall 122 from side to side can form any of a number of potential geometric shapes.

Figure 13B:
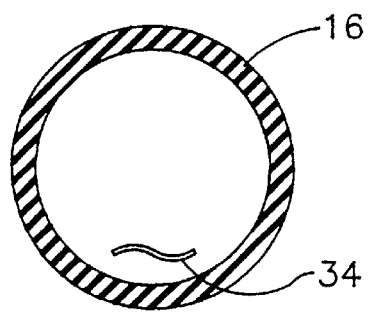
FIG. 13B is a cross-sectional view of a second embodiment of the pressure member.

FIG. 13B illustrates an embodiment in which the tensile member 34 is inside the pressure member 16. The tensile member 34 can be formed of any inextensible material, including wire, fabric, or polymer. We have found that a polyester ribbon has advantageous properties.

Figure 13C:
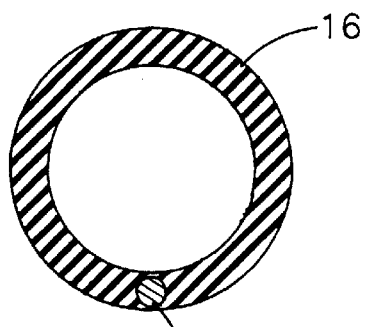
FIG. 13C is a cross-sectional view of the third embodiment of the pressure member.

FIG. 13C illustrates an embodiment in which the tensile member 34 is located on or in the wall of the pressure member 16. The tensile member 34 can be fully embedded, partially embedded, or adhered to the inside wall or the outside wall of the pressure member 16. This can be done by coextrusion of the tensile member 34 with the pressure member 16, or by subsequent welding or adhesive bonding to the pressure member 16.

Figure 13D:
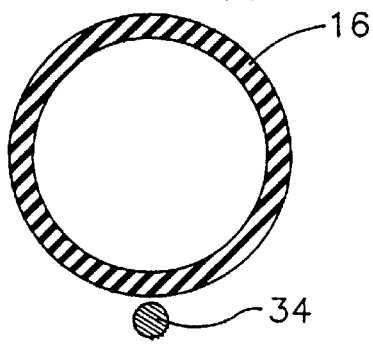
FIG. 13D is a cross-sectional view of a fourth embodiment of the pressure member.

In yet another embodiment, as illustrated in FIG. 13D, the tensile member 34 is located external to the pressure member 16 as illustrated in FIG. 13D. In this embodiment, the pressure member 16 assumes a curved or arcuate shape, while the tensile member forms a straight line between the two ends 12, 14 of the infuser 10. This embodiment has the advantage of reducing the risk of premature voiding of the infuser 10 even if one of the ends 12, 14 approaches the urethra, and also of providing a grasping point for subsequent removal of the infuser 10, taking the place of the capture loop 36.

Figure 13E:
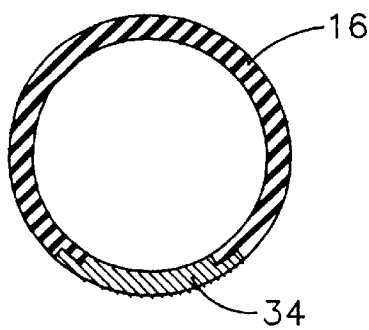
FIG. 13E is a cross-sectional view of a fifth embodiment of the pressure member.

FIG. 13E illustrates an embodiment in which the tensile member 34 comprises a different material from the rest of the pressure member 16. The tensile member 34 may, for example, be a relatively inextensible material by comparison to the remainder of the pressure member 16. It may be welded or bonded to the pressure member 16, or, preferably, it is coextruded with the material forming the pressure member 16. If silicone is used for the pressure member 16, for example, a more highly cross-linked, less extensible silicone may be coextruded with the remainder of the pressure member 16, forming a part of the wall of the pressure member 16. Alternatively, it is possible to use a material that is more extensible than the remainder of the pressure member 16, in which case the coextruded material will stretch more than the remaining pressure member and the curvature will be away from the coextruded material.

It should be recognized that there are various equivalent methods for deforming an infuser subsequent to implantation. The present invention should not be interpreted so narrowly as to avoid other shape-changing techniques.

FIG. 14 is a schematic representation of an alternative shape-changing technique. In this embodiment, a tensile member 34 connects the proximal and distal ends of the infuser 10. The tensile member may be axially shortened, with respect to the infuser 10, as illustrated in FIG. 15. In the illustrated embodiment, a ratchet mechanism 124 allows the tensile member 34 to be pulled out of an opening in the infuser 10 and to lock in that short position. An ultimate coil shape is illustrated in FIG. 15. However, depending upon the geometry of the infuser 10 and the location of the tensile member inside or outside of the infuser 10, the ultimate shape can be circular, supercoiled, arcuate, or any of various other desirable configurations.

Figure 16A:
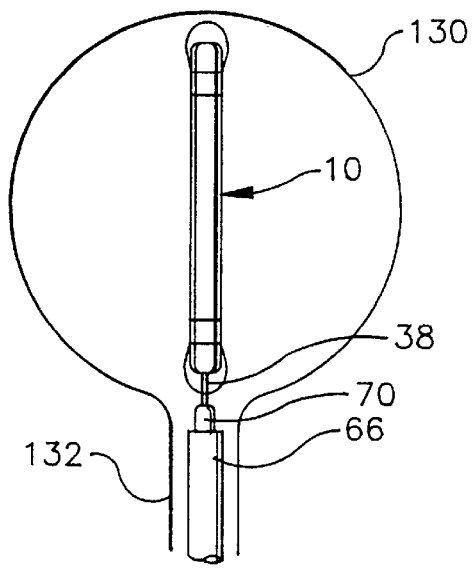
FIG. 16A is a schematic cross-sectional view of the mammalian bladder, illustrating placement of the infuser in the bladder.
Figure 16B:
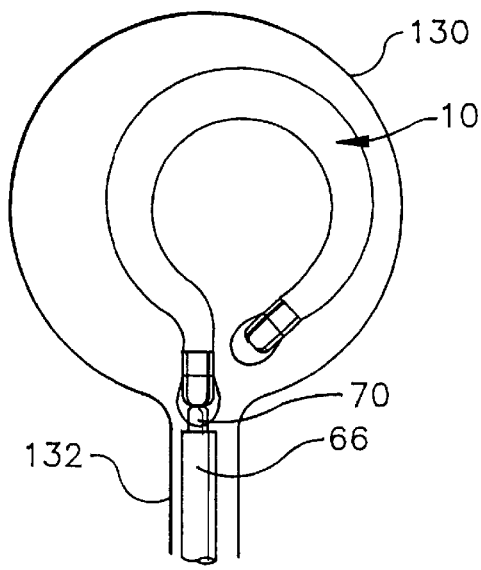
FIG. 16B is a schematic cross-section of the mammalian bladder, illustrating extracorporeal inflation or filling of the infuser with a drug while the infuser is within the bladder.
Figure 16C:
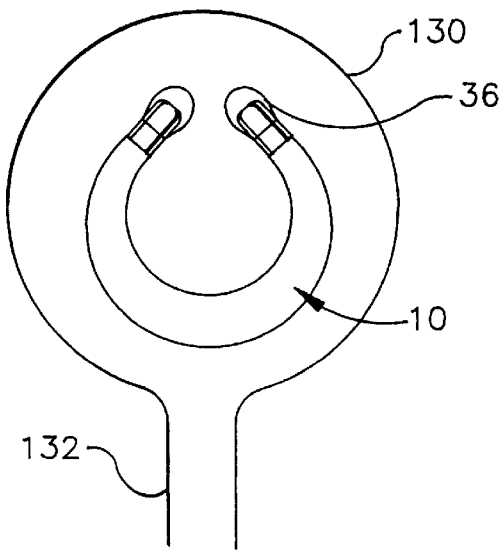
FIG. 16C is a schematic cross-section of the mammalian bladder, illustrating the infuser of the present invention floating freely within the bladder.

The method of the present invention is further illustrated in FIGS. 16A–16E. In FIG. 16A, the infuser 10 is inserted into the bladder 130 of the patient through the urethra 132 utilizing an outer sheath 66, and an extender 70. A hypodermic needle 38 is inserted through the outer sheath 66 and the extender 70 into the septum 42 of the infuser 10. FIG. 16B illustrates filling of the infuser 10 through a cannula or other fluid carrying device within the extender 70. Note that the infuser 10 assumes an arcuate or circular shape upon filling. After filling is completed, the needle 38 is withdrawn, letting the infuser 10 float freely within the bladder 130, as illustrated in FIG. 16C.

Alternatively, the infuser 10 can be tethered to the bladder wall using any of a variety of conventional tethering means, including sutures, staples, and adhesives. Installation and removal of the tethering means can be accomplished in a number of ways, including cystoscopically. To help facilitate removal of the device, dissolvable sutures can also be used. In addition, a layer of pentosanpolysulfate, can be applied to the tethering means, especially when non-dissolvable tethering means are used, such as a non-dissolvable suture. Additional information regarding the pentosanpolysulfate coating may be found in U.S. patent application Ser. No. 08/942,972, filed Oct. 3, 1997, entitled "PENTOSAN-POLYSULFATE COATING FOR MEDICAL DEVICES" which is a file wrapper continuation of a parent U.S. patent application Ser. No. 08/642,391, the disclosure of which is incorporated herein by reference.

After the substance or drug has been infused, the infuser 10 can either be refilled for additional intravesical delivery of drug or the infuser can be removed from the patient and replaced with another infuser 10 as needed. Refilling can be accomplished in a fashion similar to that of filling. The capture loop 36 or other capture arrangements can be used to manipulate the infuser 10 within the bladder 130 during refilling.

Figure 16D:
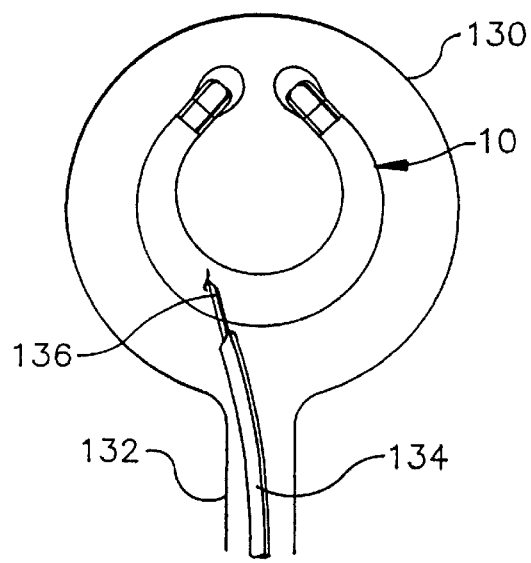
FIG. 16D is a schematic cross-section of the mammalian bladder, illustrating deflation of the infuser within the bladder.

FIG. 16D illustrates one technique for removal of the infuser after the drug has been depleted or the treatment has run its course. A cystoscope 134 is introduced into the bladder 130 of the patient and a scalpel, a needle or other rupturing or cutting tool 136 is utilized to puncture or rupture the infuser 10, thereby releasing the internal pressure to allow the infuser to deflate to an unfilled state. If desired, the remaining drug within the bladder can be flushed or otherwise withdrawn if release of a substantial quantity of drug would not be well tolerated. Alternatively, the infuser can be emptied by activation of a releasing mechanism which allows low resistance flow through the valve assembly in order to deflate to an unfilled state prior to removal of the infuser 10 from the patient. In one preferred embodiment, the drug is withdrawn from the infuser through a conduit (such as the needle 38 and any attached tube) directly out of the bladder, so that release of a bolus dose of drug into the bladder 130 is avoided.

Figure 16E:
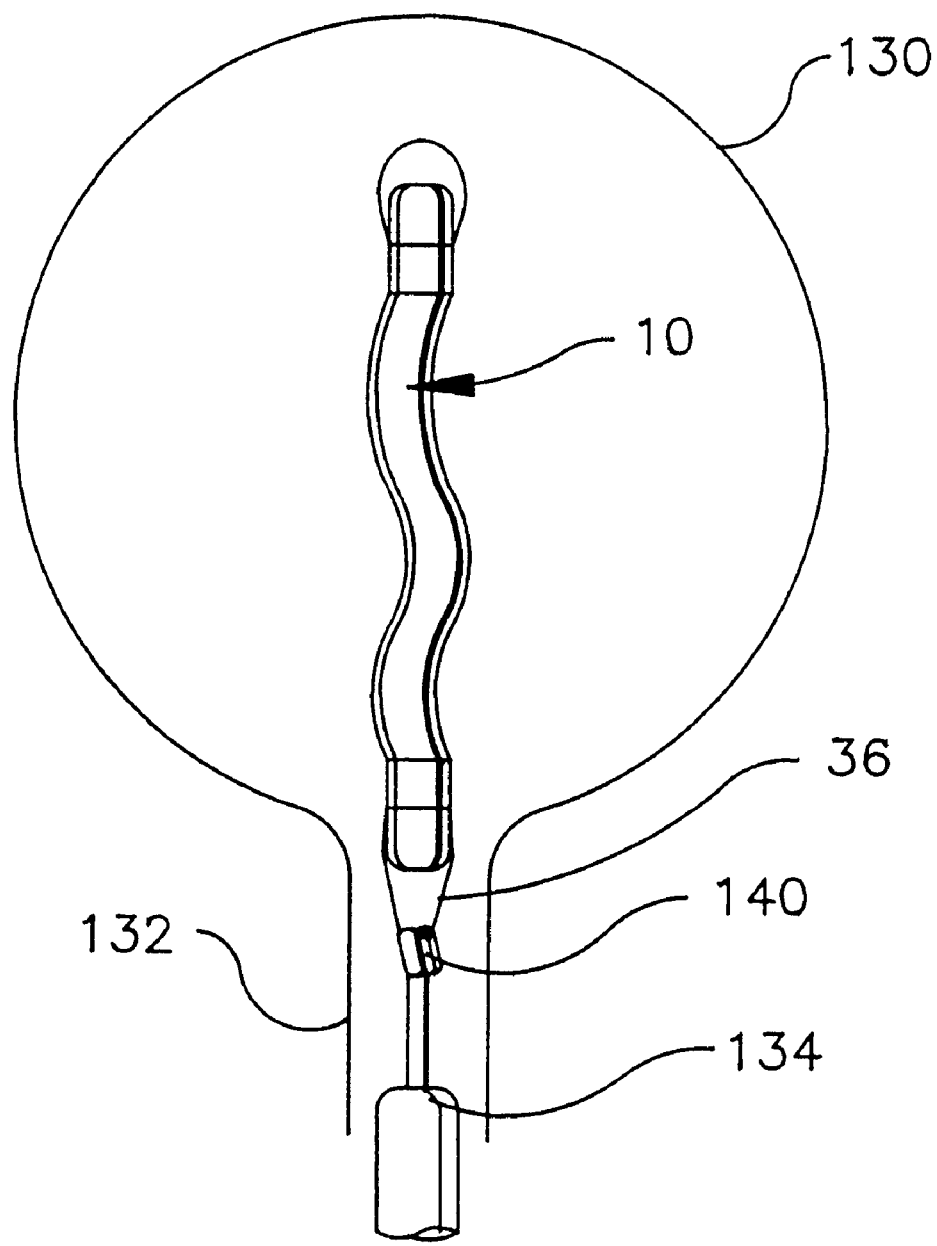
FIG. 16E is a schematic cross-section of the mammalian bladder, illustrating removal of the infuser of the present invention from the bladder.

FIG. 16E illustrates the removal of the infuser 10 from the bladder 130 of the patient. The cystoscope 134 is used to introduce a retrieval tool 140 of any suitable design. The retrieval tool 140 grasps the capture loop 36, allowing the deflated infuser 10 to be withdrawn from the bladder 130 via the urethra 132. In other embodiments, the retrieval tool may include graspers, hooks, clamps, magnets, adhesives or any other design that allows for the attachment and retrieval of the infuser.

Figure 25A:
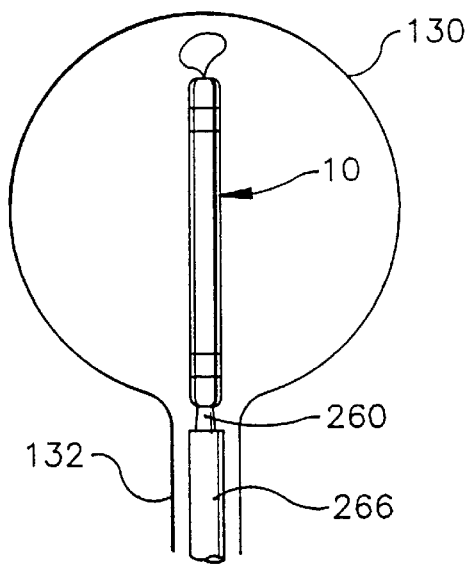
FIG. 25A is a schematic cross-sectional view of the mammalian bladder, illustrating placement of the infuser illustrated in FIG. 19 in the bladder.

The method of the present invention is further illustrated in FIGS. 25A–25D in conjunction with the infuser 10 illustrated in FIG. 19. In FIG. 25A, the infuser 10 is inserted into the bladder 130 of the patient through the urethra 132 using an introducer. After transurethral introduction of the outer sheath 266 of the introducer into the bladder, the deflated infuser 10 is passed through the outer sheath 266 into a position as illustrated in FIG. 25A. The secure coupling fitting 260 fits snugly into the opening 230 of the infuser 10. In this position, fluid drug flows through the introducer channel 264 located within the extender 262 of the introducer. Fluid flows from the introducer channel 264 through the valve entrance 246, into the fluid chamber 250 and fills or inflates the infuser 10.

Figure 25B:
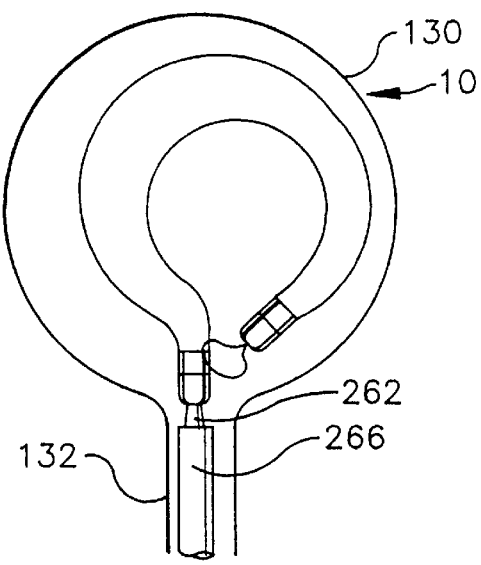
FIG. 25B is a schematic cross-section of the mammalian bladder, illustrating release of the infuser after extracorporeal inflation.

When filling is complete, the secure coupling fitting 260 is disconnected from the infuser 10 as shown in FIG. 25B to free float in the bladder of the patient. The extender 262 is retracted into the outer sheath 266 and both are then withdrawn from the patient.

Figure 25C:
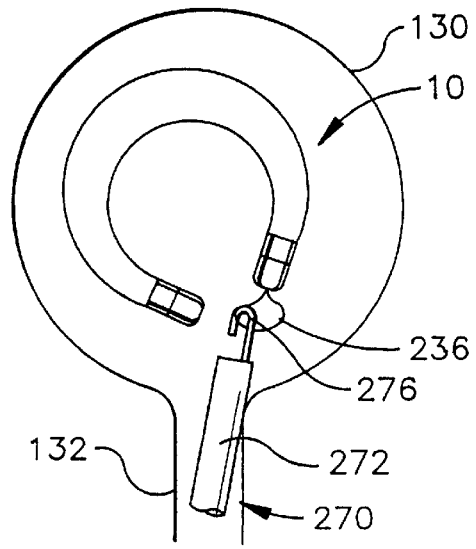
FIG. 25C is a schematic cross-section of the mammalian bladder, illustrating retrieval of the infuser from within the bladder.
Figure 25D:
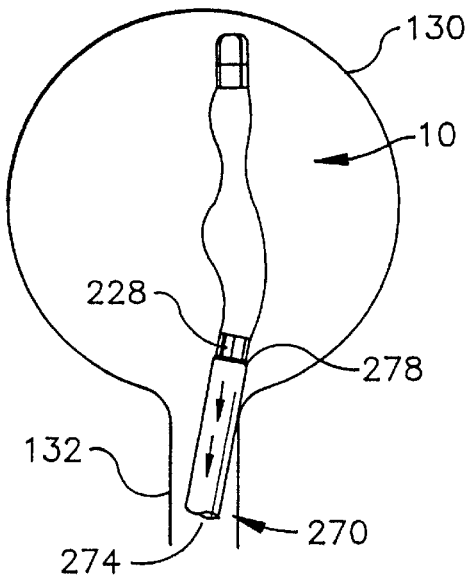
FIG. 25D is a schematic cross-section of the mammalian bladder, illustrating deflation of the infuser within the bladder.

FIG. 25C illustrates one technique for removal of the infuser after the drug has been depleted or the treatment has run its course. A retrieval device 270 is introduced into the bladder 130 of the patient. The capturing element 276 is extended from the retrieval channel 274. The capturing element 276 engages the capture member 236. The capturing element 276 is retracted into the sheathe 272. In FIG. 25D, the distal endcap bumper 228 is snuggly seated against the channel entrance 278. The remaining fluid within the infuser 10 is flowing from within the infusor 10 through the retrieval channel 274 and out of the bladder so that release of a bolus dose of drug into the bladder 130 is avoided.

Of course, it will be appreciated that the illustrated embodiments represent only one preferred method for practicing the invention. Numerous minor variations are possible without departing from the spirit of the invention. For example, instead of a needle and septum valving arrangement, any number of various valving mechanisms and latching mechanisms could be used to connect the infuser 10 to the extender 70 or the hypodermic needle 38 (or a cannula or locking member taking the place of hypodermic needle 38). Thus, the external source of fluid may be attached to the interior of the pressure member 16 via a valving mechanism, and the infuser 10 may be physically attached to and releasable from the extender 70. In addition, numerous other capture arrangements are possible besides the use of a capture loop 36. For example, a magnetic mechanism may be utilized to draw one end of the infuser 10 into sufficiently close proximity to the cystoscope 134 that capture can be effected. A basket or expanding and contracting mesh ("Chinese finger trap") apparatus may similarly be used.

In other embodiments of the invention, the collars 24, 26 or other portions of the infuser may be made radiopaque in order to facilitate visualization of the infuser by ultrasound, X-ray or other visualization means.

In one embodiment of the invention, mechanically driven, electrically driven, or osmotically driven infusion means is substituted for the pressure member 16. Alternatively, the substance or drug utilized in the invention can be impregnated into a controlled release or bioerodable material that effects a shape change upon introduction into the bladder.

In one important aspect of the invention, the entire infuser 10 or appropriate portions thereof may be coated with a biocompatible coating. A major problem that has been experienced with most devices that are left in the bladder for more than a few days is encrustation and infection. Various salts, proteins, and other materials in the urine can rapidly build up on foreign objects left within the bladder. This, in turn, leads to irritation and difficulty in removing the device without injuring the patient. In some cases, the entire infuser 10 may be coated. In other cases, only appropriate portions of the infuser 10 are coated such as the proximal end cap 20 and distal end cap 22

We have discovered that certain polysaccharide coatings can reduce or even prevent encrustation. These coatings include pentosanpolysulfate, heparin and other sulfonated polysaccharides or drugs. Silicone and many biocompatible plastics will not readily accept a coating of these biocompatible materials. We have found that this obstacle can be overcome by surface pretreatment of the device by any of a number of surface modification techniques. These include corona discharge, ionic discharge, chemical etching such as by treatment with a strong base, and plasma treatment. One technique is disclosed in previously incorporated U.S. patent application Ser. No. 08/942,972, filed Oct. 3, 1997, entitled "PENTOSANPOLYSULFATE COATING FOR MEDICAL DEVICES."

An infuser according to the invention may be used as a self contained means of delivering therapeutic agents to a variety of functioning organs within a living organism. The infuser may be introduced into the functioning organ through a natural orifice or created orifice.

In one embodiment, the device is inserted into the patient containing a therapeutic or diagnostic agent in condensed form. When the device is within the bladder, it is filled with a reconstitution agent which causes a shape change in the device and activates the agent within the device. For example, the device may be filled with a saline solution which activates a drug in power form within the device.

In the methods of using the device falling within the scope of the present invention, a wide variety of drugs or other substances, including contrast agents can be administered to the bladder. These drugs or other substances can be provided in a variety of forms, including liquids and hydratable powders. These drugs and other materials can be used for a variety of purposes, including the treatment of urinary incontinence, urinary tract cancer, urinary tract infections, inflammatory conditions of the urinary tract, and to provide pain relief.

Urinary incontinence, including urge incontinence and neurogenic incontinence, can be treated using the device of the present invention. Preferably, anticholinergic and/or antispasmodic agents are used. In addition, antimuscarinic agents, β–2 agonists, norepinephrine uptake inhibitors, serotonin uptake inhibitors, calcium channel blockers, potassium channel openers, and muscle relaxants can also be used. Suitable drugs for the treatment of incontinence include oxybutynin, S-oxybutynin, emepronium, verapamil, imipramine, flavoxate, atropine, propantheline, tolterodine, rociverine, clenbuterol, darifenacin (Pfizer, Europe, USA, Japan), terodiline, trospium, hyoscyamin, propiverine, desmopressin, vamicamide (Fujiwara Co., Japan), YM-46303 (Yamanouchi Co., Japan), lanperisone (Nippon Kayaku Co., Japan), inaperisone, NS-21 (Nippon Shinyaku Orion, Formenti, Japan/Italy), NC-1800 (Nippon Chemiphar Co., Japan), ZD-6169 (Zeneca Co., United Kingdom), and stilonium iodide. In addition, the substance released from the device may used for diagnostic purposes.

Urinary tract cancer, such as bladder cancer and prostate cancer, may be treated using the device of the present invention by infusing antiproliferative agents, cytotoxic agents and/or chemotherapeutics. Suitable drugs for the treatment of urinary tract cancer include Bacillus Calmette Guerin (BCG) vaccine, cisplatin, doxorubicin, methotrexate, vinblastine, thiotepa, mitomycin, fluorouracil, leuprolide, flutamide, diethylstilbestrol, estramustine, megestrol acetate, cyproterone, flutamide, and cyclophosphamide. Treatment of urinary tract cancer can be effected in conjunction with other conventional cancer treatment techniques, including surgical excision, and radiation therapy.

In a similar manner, infections involving the bladder, the prostate, and the urethra, can be treated using the device of the present invention. Antibiotics, antibacterial, antifungal, antiprotozoal, antiviral and other antiinfective agents can be administered for treatment of such infections. Suitable drugs for the treatment of such infections include mitomycin, ciprofloxacin, norfloxacin, ofloxacin, methanamine, nitrofurantoin, ampicillin, amoxicillin, nafcillin, trimethoprim, sulfa, trimethoprim-sulfamethoxazole, erythromycin, doxycycline, metronidazole, tetracycline, kanamycin, penicillins, cephalosporins, and aminoglycosides.

Inflammatory conditions such as interstitial cystitis, prostatitis, and urethritis can also be treated using the device of the present invention. Drugs having an antiinflammatory and/or coating effect are useful in this regard. Suitable drugs include dimethyl sulfoxide (DMSO), heparin, pentosanpolysulfate sodium, and flavoxate.

The device of the present invention can also be used to provide pain relief to the patient. In this regard, a variety of anesthetic and/or analgesic agents can be infused through the device of the present invention, including lidocaine hydrochloride, procaine hydrochloride, salicyl alcohol, tetracaine hydrochloride, phenazopyridine hydrochloride, acetaminophen, acetylsalicylic acid, flufenisal, ibuprofen, indoprofen, indomethacin, naproxen, codeine, oxycodone, and fentanyl citrate.

The device of the present invention can also be used to administer drugs and other materials for a variety of other purposes. For example, the device can be used to administer glycine for purposes such as bladder irrigation.

The treatment method of the present invention provides for slow, continuous, intermittent or periodic release of a desired quantity of drug over a desired period of time. In one preferred embodiment, the volume of the infuser is such that it can deliver the desired dose of drug over an extended period of time, e.g., 24 hours, 5 days, 10 days, 15 days or even 20, 25, 30, 60, 90 days or more. The rate of delivery in order to accomplish this result is relatively slow. Thus, the present invention contemplates the drug delivery rates within the range of 0.1, 1, 5, 10, 25, 50, 75, 100, 150, or 200 $\mu$l/hr. Of course, slower or faster delivery rates can be selected depending upon the drug being delivered and the disease being treated. In any particular situation, and for any particular disease state, the concentration of the drug and the rate of delivery can be selected by the physician based on conventional methodologies.

The infuser device of the present invention has been successfully tested in adult pigs. The practice of the present invention is illustrated in the following non-limiting examples.

EXAMPLE 1

Female swine in the weight range 40–45 kg were sedated using 10 ml of ketamine chloride and 3 ml of atropine. Upon achieving proper sedation, an endotrachial tube was placed in the animal's airway and the animal maintained on isoflurane gas between 0.5% and 4% as an intraoperative anesthesia. Following standard sterile procedures, a 21 Fr Storz cystoscope was used to visualize and position a 0.038 inch guidewire in the bladder of the pig. Removing the cystoscope, a 23 Fr introducer sheath and obturator were passed over the guidewire into the bladder of the animal. The obturator and guidewire were removed. An infuser mounted on a 23 gauge needle at the distal end of a launcher tube was placed through the introducer sheath into the bladder. A 60 cc syringe mounted in an infusion assist device was attached to the proximal end of the launcher tube through a section of tubing. The tubing was primed before attachment to purge all air from the system. The 60 cc syringe was filled with 35 cc of tritium labeled sodium pentosanpolysulfate drug. Total counts of the radioactivity of the tritium labeled drug for the 35 cc were measured from a 100 $\mu$l sample of drug using a Beckman scintillation counter prior to beginning the study. The infuser was positioned in the bladder such that the majority of the infuser extended beyond the introducer sheath. Thirty cc of drug was injected into the infuser and the infuser expanded into the filled state. The 23 gauge needle was withdrawn from the infuser, and the introducer sheath and launcher assemblies were removed from the patient, allowing the infuser to float freely within the bladder. The pigs were allowed to recover from the anesthesia and were returned to their cages.

The total urine output from the pigs was collected and measured daily for thirty days. Total urine output varied between 1.75–3.5 liters/day. A 100 $\mu$l sample of urine was taken from each daily collection and placed in a Beckman scintillation counter to determine the number of radioactive counts within the sample. The measurement gave the total counts in the daily collection which was compared to the original measurement of total counts made at the beginning of the study to determine the amount of drug in the daily collection. Average counts of a 100 $\mu$l sample from a daily collection typically measured 750–1000 counts. In this manner, it was determined the output of the device varied between 2 cc per day at the beginning of the study to 0.75 cc per day on the thirtieth day of the study. At the end of the thirty days, the animal was sacrificed by injection of 12 ml of Beuthanasia-D and its bladder removed. Histological specimens were taken from the neck, trigone, base, and dome areas of the bladder, fixed in formaldehyde, imbedded in parafin, sectioned, and stained with H&E. Examination of the sections showed normal tissue with no apparent injury caused by the infuser.

EXAMPLE 2

The infuser may be used in human patients to treat neurogenic bladder disease or urge incontinence using anticholinergic or antimuscarinic drugs such as oxybutynin or flavoxate. A patient is prepared in the dorsal lithotomy position. Standard cystoscopic procedures are performed on the patient using local anesthesia and accepted sterile techniques. An introducer sheath and an obturator are transurethrally positioned to allow access to the bladder. To minimize patient discomfort, water soluble lidocaine jelly is used to facilitate the passage of the introducer sheath/obturator within the urethra. The obturator is removed and the infuser is passed through the introducer into the bladder. The infuser is connected to a source of therapeutic agent through the introducer sheath. The infuser is filled with about 30 cc of the therapeutic agent from the source. The source of therapeutic agent may comprise a hypodermic needle which penetrates a septum in the infusor or a pressure source which opens a check valve in the infuser. After filling is complete, the source is uncoupled from the infuser so that the infuser floats freely within the bladder. The introducer is removed from the urethra.

The infuser remains in the patient's bladder for 30 days infusing the therapeutic agent to relieve the symptoms of urge incontinence or neurogenic bladder disease without the side effects associated with alternate drug administration routes such as oral or intravenous methods. After 30 days, the patient is prepared in a similar fashion as described above. A cystoscope is inserted through the urethra into the bladder and the infuser is located by visualization. Any residual therapeutic agent remaining in the infuser is removed to reduce the profile of the infuser to facilitate its removal. The removal of the therapeutic agent may be accomplished by passing a needle or cutting tool though a working channel of the cystoscope to rupture the infuser.

Alternatively, a tool to access a release mechanism in the infuser may purge the contents of the infuser. The bladder may be flushed in order to remove the released drug if necessary. A retrieval tool is passed through a working channel of the cystoscope. The retrieval tool grasps the infuser and removes the infuser from the bladder. The infuser and cystoscope are removed from the urethra. A subsequent infuser may be introduced into the bladder following the procedure described above if additional therapy is necessary.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims.

What is claimed is:

1. A method of dispensing medication within a body comprising:

implanting a substantially empty resilient reservoir having a generally elongated shape into the body;

transferring medication into the resilient reservoir while it is within the body, wherein the receipt of said medication causes the resilient member to assume a shape which is at least partially arcuate; and dispensing medication from the reservoir into the body over a substantially controlled period of time.

2. The method of claim 1, wherein said medication is an incontinence-treating drug.

3. The method of claim 1, wherein said medication is used to treat urge incontinence.

4. The method of claim 1, wherein said medication is used to treat pain or neuralgia.

5. The method of claim 1, wherein said medication is an antibiotic.

6. The method of claim 1, wherein said medication is used to treat cystitis.

7. The method of claim 1, wherein said medication is an anti-cancer drug.

8. The method of claim 1, further comprising the step of removing the resilient reservoir from the bladder after said infusing step.

9. A method of dispensing medication within a body comprising:

implanting a substantially empty infusion device into the body, the infusion device configured to contain a medication and comprising an elastomeric portion which defines a substantially elongated shape when empty;

introducing medication into the infusion device;

expanding the elastomeric portion as medication is added to the infusion device;

constraining a portion of the elastomeric portion as said elastomeric portion expands such that the expanded elastomeric portion defines a nonlinear profile; and dispensing medication from the infusion device into the body.

10. The method of claim 9, wherein said medication is an incontinence-treating drug.

11. The method of claim 9, wherein said medication is used to treat urge incontinence.

12. The method of claim 9, wherein said medication is used to treat pain or neuralgia.

13. The method of claim 9, wherein said medication is an antibiotic.

14. The method of claim 9, wherein said medication is used to treat cystitis.

15. The method of claim 9, wherein said medication is an anti-cancer drug.

16. The method of claim 9, further comprising the step of removing the infusion device from the bladder after said infusing step.

* * * * *